US006207147B1

(12) United States Patent
Hiserodt et al.

(10) Patent No.: US 6,207,147 B1
(45) Date of Patent: Mar. 27, 2001

(54) CANCER IMMUNOTHERAPY USING TUMOR CELLS COMBINED WITH MIXED LYMPHOCYTES

(75) Inventors: John C. Hiserodt, Huntington Beach; James A. Thompson, Aliso Viejo; Gale A. Granger, Laguna Beach, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 08/948,939

(22) Filed: Oct. 10, 1997

Related U.S. Application Data

(60) Provisional application No. 60/028,548, filed on Oct. 11, 1996.

(51) Int. Cl.$^7$ .............................. A01N 63/00; C12N 5/06; C12N 5/08; C12N 5/02

(52) U.S. Cl. ........................ 424/93.1; 424/93.3; 435/363; 435/366; 435/372; 435/373; 435/347; 435/374

(58) Field of Search .................................. 424/93.1, 93.3; 435/325, 277.1, 363, 366, 372, 373, 347, 374

(56) References Cited

U.S. PATENT DOCUMENTS

| 5,192,537 | 3/1993 | Osband . |
| 5,484,596 | 1/1996 | Hanna, Jr. et al. . |
| 5,569,585 | 10/1996 | Goodwin et al. . |

FOREIGN PATENT DOCUMENTS

| WO 95/16775 | 6/1995 | (WO) . |
| WO 95/31107 | 11/1995 | (WO) . |
| WO 96/05866 | 2/1996 | (WO) . |
| WO 96/29394 | 9/1996 | (WO) . |
| WO 98/04282 | 2/1998 | (WO) . |

OTHER PUBLICATIONS

Albright et al., "Immunogenetic control of brain tumor growth in rats" *Cancer Res.* (1977)37:2512–2521.
Berd et al., "Treatment of metastatic melanoma with an autologous tumor–cell vaccine: Clinical and immunologic results in 64 patents" *J. Clin. Oncol.* (1990) 8:1858–1867.
Chang et al., "Phase I clinical trial of allogeneic mixed lymphocyte culture (cytoimplant) delivered by endoscopic ultrasound (EUS)–guided fine needle injection (FNI) in patients with advanced pancreatic carcinoma" *Gastroenterology* (1997) 112(4):A546, Abstract only.
Colombo, "Tumor cells engineered to produce cytokines or cofactors as cellular vaccines: do animal studies really support clinical trials?" *Cancer Immunol. Immunother.* (1995) 41:265–270.
Dillman et al., "Establishing in vitro cultures of autologous tumor cells for use in active specific immunotherapy" *J. Immunother.* (1993) 14:65–69.

Dranoff et al., "Vaccination with irradiated tumor cells engineered to secrete murine granulocyte–macrophage colony–stimulating factor stimulates potent, specific, and long lasting anti–tumor immunity" *Proc. Natl. Acad. Sci. USA* (1993) 90:3539–3543.
Gately, "In vitro studies on the cell–mediated immune response to human brain tumors. I. Requirement for third–party stimulator lymphocytes in the induction of cell–mediated cytotoxic responses to allogeneic cultured gliomas" *J. Natl. Cancer Inst.* (1982) 19: 1245–1254.
Golumbek et al., "Herpes simplex–1 virus thymidine kinase gene is unable to completely eliminate live, nonimmunogenic tumor cell vaccines" *J. Immunother.* (1992) 12:224–230.
Kondo et al., "Rationale for a novel immunotherapy of cancer with allogeneic lymphocyte infusion" *Med. Hypotheses* (1984) 15:241–277.
Kruse et al., "Artificial–capillary–system development of human alloreactive cytotoxic T–lymphocytes that lyse brain tumors" *Biotechnol. Appl. Biochem.* (1997) 25: 197–205.
Kruse et al., "Cellular therapy of brain tumors: Clinical trials" *Advances in Neuro–Oncology II*, (Kornblith et al., eds.), Futura Publishing Company, Inc., Armonk, NY, (1997) Ch. 22, pp. 487–504.
Kruse et al., "Immune therapy of recurrent malignant gliomas: Intracavitary allogeneic cytotoxic T lymphocytes and human recombinant interleukin–2" *FASEB J.* (1996) 10(6):A1413 (abstract 2387).
Kruse et al., "Migration of activated lymphocytes when adoptively transferred into cannulated rat brain" *J. Neuroimmunol.* (1994) 55:11–21.
Leshem et al., "In vitro elicitation of cytotoxic response against a nonimmunogenic murine tumor by allosensitization" *Cancer Immunol. Immunother.* (1984) 17:117–123.
Lillehei et al., "Long–term follow–up of patients with recurrent malignant gliomas treated with adjuvant adoptive immunotherapy" *Neurosurgery* (1991) 28:16–23.

(List continued on next page.)

Primary Examiner—Geetha P. Bansal
(74) Attorney, Agent, or Firm—Carol L. Francis; Bozicevic, Field & Francis, LLP.

(57) ABSTRACT

This invention comprises cellular vaccines and methods of using them in cancer immunotherapy, particularly in humans. The vaccines comprise stimulated lymphocytes allogeneic to the subject being treated, along with a source of tumor-associated antigen. The allogeneic lymphocytes can be stimulated by combining or coculturing them with leukocytes obtained from the subject to be treated or from another third-party donor. Tumor antigen may be provided in the form of primary tumor cells, tumor cell lines or tumor extracts prepared from the subject. Stimulated allogeneic lymphocytes and tumor antigen are combined and administered at a site distant from the primary tumor, in order to prime or boost a systemic cellular anti-tumor immune response. This approach overcomes the natural refractory nature of the immune system to stimulation by tumor antigens, generating a host response and potentially improving the clinical outcome.

34 Claims, 11 Drawing Sheets

OTHER PUBLICATIONS

Mitchell et al., "Active specific immunotherapy of melanoma with allogeneic cell lysates. Rationale, results, and possible mechanisms of action" *Ann. N.Y. Acad. Sci.* (1993) 690:153–166.

Redd et al., "Allogeneic tumor–specific cytotoxic T lymphocytes" *Cancer Immunol. Immunother.* (1992) 34:349–354.

Rosenberg et al., "Gene transfer into humans—Immunotherapy of patients with advanced melanoma, using tumor–infiltrating lymphocytes modified by retroviral gene transduction" *New Engl. J. M. ed.* (1990) 323:570–578.

Santin et al., "Development and characterization of an IL–4–secreting human ovarian carcinoma cell line" *Gynecol. Oncol.* (1995) 58:230–239.

Santin et al., "Development and characterization of an interleukin–2–transduced human ovarian tumor vaccine not expressing major histocompatibility complex molecules" *Am. J. Obst. Gynecol.* (1996) 174:633–639.

Santin et al., "Development and in vitro characterization of a GM–CSF secreting human ovarian carcinoma tumor vaccine" *Int. J. Gynecol. Cancer* (1995) 5:401–410.

Schirrmacher et al., "Workshop: Active specific immunotherapy with tumor cell vaccines" *J. Cancer Res. Clin. Oncol.* (1995) 121:487–489.

Schlitz et al., "Movement of allogeneic cytotoxic T lymphocytes (aCTL) infused into the parietal region of 9L gliosarcoma bearing brain" *Proc. Amer. Assoc. Cancer Res.* (1995) 36:458 (abstract No. 2727).

Strausser et al., "Lysis of human solid tumors by autologous cells sensitized in vitro to alloantigens" *J. Immunol.* (1981) 127(1):266–271.

Zarling et al., "Generation of cytotoxic T lymphocytes to autologous human leukemia cells by sensitization to pooled allogeneic normal cells" *Nature* (1978) 274: 269–271.

CANCER IMMUNOTHERAPY USING TUMOR CELLS COMBINED WITH MIXED LYMPHOCYTES

REFERENCE TO RELATED APPLICATIONS

This application claims the priority benefit of provisional U.S. patent application Ser. No. 60/028,548, filed Oct. 11, 1996, which is hereby incorporated herein by reference in its entirety.

FIELD OF THE INVENTION

The present invention relates generally to the fields of cellular immunology and cancer therapy. More specifically, it relates to the generation of an anti-tumor immune response in a subject (particularly a human) by administering a cellular vaccine, comprising inactivated tumor cells and stimulated immune cells, such as may be generated in a mixed lymphocyte culture.

BACKGROUND

In spite of numerous advances in medical research, cancer remains a leading cause of death throughout the developed world. Non-specific approaches to cancer management, such as surgery, radiotherapy and generalized chemotherapy, have been successful in the management of a selective group of circulating and slow-growing solid cancers. However, many solid tumors are considerably resistant to such approaches, and the prognosis in such cases is correspondingly grave.

One example is brain cancer. Each year, approximately 15,000 cases of high grade astrocytomas are diagnosed in the United States. The number is growing in both pediatric and adult populations. Standard treatments include cytoreductive surgery followed by radiation therapy or chemotherapy. There is no cure, and virtually all patients ultimately succumb to recurrent or progressive disease. The overall survival for grade IV astrocytomas (glioblastoma multiforme) is poor, with ~50% of patients dying in the first year after diagnosis. Because these tumors are aggressive and highly resistant to standard treatments, new therapies are needed.

An emerging area of cancer treatment is immunotherapy. The general principle is to confer upon the subject being treated an ability to mount what is in effect a rejection response, specifically against the malignant cells. There are a number of immunological strategies under development, including: 1. Adoptive immunotherapy using stimulated autologous cells of various kinds; 2. Systemic transfer of allogeneic lymphocytes; 3. Intra-tumor implantation of immunologically reactive cells; and 4. Vaccination at a distant site to generate a systemic tumor-specific immune response.

The first of the strategies listed above, adoptive immunotherapy, is directed towards providing the patient with a level of enhanced immunity by stimulating cells ex vivo, and then readministering them to the patient. The cells are histocompatible with the subject, and are generally obtained from a previous autologous donation.

One approach is to stimulate autologous lymphocytes ex vivo with tumor-associated antigen to make them tumor-specific. Zarling et al. (1978) *Nature* 274:269–71 generated cytotoxic lymphocytes in vitro against autologous human leukemia cells. Lee et al. (1996) abstract, Gastroenterology conducted an in vitro mixed lymphocyte culture with inactivated leukemic blast cells and autologous lymphocytes, and generated effector T lymphocytes cytotoxic for a tumor antigen on autologous blast cells. An MHC D-locus incompatibility was thought to be necessary to provide proper help in the lymphocyte culture. Lesham et al. (1984) *Cancer Immunol Immunother.* 17:117–23 developed cytotoxic responses in vitro against murine thymoma cells by allosensitization.

Gately et al. (1982) *J. Natl. Cancer Inst.* 69:1245–54 found that 5 out of 9 human glioma cell lines did not elicit allogeneic cytolytic lymphocyte responses in ex vivo cultures. However, if inactivated, allogeneic lymphocytes were provided as stimulator cells in the cultures, tumor-specific cytolytic T lymphocytes and non-specific non-T effectors were generated to 4 of the nonstimulatory lines. In U.S. Pat. No. 5,192,537, Osband suggests activating a tumor patient's mononuclear cells by culturing them ex vivo in the presence of tumor cell extract and a non-specific activator like phytohemagglutinin or IL-1, and then treating the culture to deplete suppresser cell activity.

Despite these experimental observations, systemic administration of ex vivo-stimulated autologous tumor-specific lymphocytes has not become part of standard cancer therapy.

Autologous lymphocytes and killer cells may also be stimulated non-specifically. In one example, Fc receptor expressing leukocytes that can mediate an antibody-dependent cell-mediated cytotoxicity reaction are generated by culturing with a combination of IL-2 and IFN-γ (U.S. Pat. No. 5,308,626). In another example, peripheral blood-derived lymphocytes cultured in IL-2 form lymphokine-activated killer (LAK) cells, which are cytolytic towards a wide range of neoplastic cells, but not normal cells. LAK are primarily derived from natural killer cells expressing the CD56 antigen, but not CD3. Such cells can be purified from peripheral blood leukocytes by IL-2-induced adherence to plastic (A-LAK cells; see U.S. Pat. No. 5,057,423). In combination with high dose IL-2, LAK cells have had some success in the treatment of metastatic human melanoma and renal cell carcinoma. Rosenberg (1987) *New Engl. J Med.* 316:889–897. This strategy is labor-intensive, costly, and not suited to all patients. Schwartz et al. (1989) *Cancer Res.* 49:1441–1446 showed that A-LAK cells are superior to LAK cells at reducing lung and liver metastases of breast cancer in experimental animal models, but this was not curative and there were no long-term survivors.

For examples of trials conducted using LAK in the treatment of brain tumors, see Merchant et al. (1988) *Cancer* 62:665–671 & (1990) *J. Neuro-Oncol.* 8:173–198; Yoshida et al. (1988) *Cancer Res.* 48:5011–5016; Barba et al. (1989) *J. Neurosurg.* 70:175–182; Hayes et al. (1988) *Lymphokine Res.* 7:337–345; and Naganuma et al (1989) *Acta Neurochir.* (Wien) 99:157–160. Another study proposes therapy for recurrent high-grade glioma using autologous mitogen-activated and IL-2 stimulated (MAK) killer lymphocytes, in combination with IL-2. Jeffes et al. (1991) *Lymphokine Res.* 10:89–94. While none of these trials was associated with serious clinical complications, efficacy was only anecdotal or transient. Induction of tumor-specific immunity in patients receiving such treatments has not been shown.

Another form of adoptive therapy using autologous cells has been proposed based on observations with tumor-infiltrating lymphocytes (TIL). TILs are obtained by collecting lymphocyte populations infiltrating into tumors, and culturing them ex vivo with IL-2. Finke et al. (1990) *Cancer Res.* 50:2363–2370 have characterized cytolytic activity of CD4+ and CD8+ TIL in human renal cell carcinoma. TILs have activity and tumor specificity superior to LAK cells, and have been experimentally administered, for example, to humans with advanced melanoma. Rosenberg et al. (1990) *New Engl. J. Med.* 323:570–578. The effector population within TILs may be cytotoxic T lymphocytes (CTL) which are primed to be tumor-specific in the host and are devoid of lytic granules, and become transformed into cytolytic lymphoblasts when stimulated in culture. Berke et al.(1988) *J. Immunol.* 129:303 ff. Unfortunately, TILs can only be prepared in sufficient quantity to be clinically relevant in a limited number of tumor types. These strategies remain experimental, especially in human therapy.

The second of the strategies for cancer immunotherapy listed earlier is adoptive transfer of allogeneic lymphocytes. The rationale of this experimental strategy is to create a general level of immune stimulation, and thereby overcome the anergy that prevents the host's immune system from rejecting the tumor. Strausser et al. (1981) *J. Immunol.* Vol. 127, No. 1 describe the lysis of human solid tumors by autologous cells sensitized in vitro to alloantigens. Zarling et al. (1978) *Nature* 274:269–71 demonstrated human anti-lymphoma responses in vivo following sensitization with allogeneic leukocytes. Kondo et al. (1984) *Med Hypotheses* 15:241–77 observed objective responses of this strategy in 20–30% of patients, and attributed the effect to depletion of suppressor T cells. The studies were performed on patients with disseminated or circulating disease. Even though these initial experiments were conducted over a decade ago, the strategy has not gained general acceptance, especially for the treatment of solid tumors.

The third of the immunotherapy strategies listed earlier is intra-tumor implantation. This is a strategy directed at delivering effector cells directly to the site of action. Since the transplanted cells do not circulate, they need not be histocompatible with the host. Intratumor implantation of allogeneic cells may promote the ability of the transplanted cells to react with the tumor, and initiate a potent graft versus tumor response.

Kruse et al. (1990) *Proc. Natl. Acad. Sci U.S.A.* 87:9577–9581 demonstrated that direct intratumoral implantation of allogeneic cytotoxic T lymphocytes (CTL) into brain tumors growing in Fischer rats resulted in a significant survival advantage over other populations of lymphocytes, including syngeneic CTL, LAK cells, adherent-LAK cells or IL-2 alone. Redd et al. (1992) *Cancer Immunol. Immunother.* 34:349–354 developed cytotoxic T lymphocytes specific for an allogeneic brain tumor in rats. The lymphocytes were specific for a determinant expressed only by the tumor, and were predicted to be useful for therapeutic purposes in vivo. Kruse et al. (1994) *J. Neurooncol.* 19:161–168 prepared CTLs from four MHC incompatible rat strains, and used them to treat Fischer rats bearing established 9L brain tumors. CTL were administered on a biweekly schedule, a different MHC incompatible CTL preparation being administered each time. Animals without tumor showed minimal localized brain damage. Those with tumors either showed: a) mononuclear cell infiltration, massive tumor necrosis beginning 2–4 days after treatment, and total tumor destruction by 15 days; or b) cellular infiltration, early tumor destruction, and then tumor regrowth progressing to death of the animal. Tumor regressor animals were resistant to intracranial rechallenge with viable tumor cells. Kruse et al. (1994). Intratumor CTL implants may optionally be combined with chemotherapy using cyclophosphamide. Kruse et al. (1993) *J. Neurooncol.* 15:97–112.

Despite the promise of intratumor implantation techniques, several caveats remain. For one thing, implantation is frequently performed by surgical techniques, which may be too invasive for routine maintenance. In addition, the strategy is directed at generating a local response, not at generating a systemic response that is generally necessary for protection against metastases.

The fourth of the immunotherapy strategies listed earlier is the generation of an active systemic tumor-specific immune response of host origin. The response is elicited from the subject's own immune system by administering a vaccine composition at a site distant from the tumor. The specific antibodies or immune cells elicited in the host as a result will hopefully migrate to the tumor, and then eradicate the cancer cells, wherever they are in the body.

Various types of vaccines have been proposed, including isolated tumor-antigen vaccines and anti-idiotype vaccines. Mitchell et al. (1993)*Ann. N.Y. Acad. Sci.* 690:153–166 have treated cancer patients with mechanical lysates from a plurality of allogeneic melanoma cell lines, combined with the adjuvant DETOX™. These approaches are all based on the premise that tumors of related tissue type all share a common tumor-associated antigen. For patients with tumors that did lot acquire expression of the antigen during malignant transformation, or that subsequently differentiated so as not to express it, none of these vaccines will be successful.

An alternative approach to an anti-tumor vaccine is to use tumor cells from the subject to be treated, or a derivative of such cells. For review see, Schirrmacher et al. (1995) *J. Cancer Res. Clin. Oncol.* 121:487–489. In U.S. Pat. No. 5,484,596, Hanna Jr. et al. claim a method for treating a resectable carcinoma to prevent recurrence or metastases, comprising surgically removing the tumor, dispersing the cells with collagenase, irradiating the cells, and vaccinating the patient with at least three consecutive doses of about $10^7$ cells. The cells may optionally be cryopreserved, and the immune system may be monitored by skin testing. This approach does not solve the well-established observations that many tumors are not naturally immunogenic. Many patients from which tumors have been resected are either tolerant or unable to respond to their own tumor antigen, even when comprised in a vaccine preparation.

Several ways of preparing autologous or syngeneic tumor cells have emerged that potentially enhance immunogenicity. Tumor cells may be combined with extracts of bacillus Calmette-Guerin (BCG) or the A60 mycobacterial antigen complex, or mixed with vaccinia virus or Newcastle Disease Virus (NDV). Guo and coworkers (WO 95/16775) suggested that tumor cells be fused with membrane components of a second cell such as a B cell that has a greater immunogenic potential.

In yet another approach, autologous or syngeneic tumor cells are genetically altered to produce a costimulatory molecule. Examples of costimulatory molecules include cell surface receptors, such as the B7-1 costimulatory molecule or allogeneic histocompatibility antigens. Other examples are secreted activators, including cytokines. For reviews see, Pardoll et al. (1992) *Curr. Opin. Immunol.* 4:619–23; Saito et al. (1994) *Cancer Res.* 54:3516–3520; Vieweg et al. (1994) *Cancer Res.* 54:1760–1765; Gastl et al. (1992) *Cancer Res.* 52:6229–6236; and WO 96/07433). Tumor cells have been genetically altered to produce TNF-α, IL-1, IL-2, IL-3, IL-4, IL-6, IL-7, IL-10, IFN-α, IFN-γ and GM-CSF. See, for example, Santin et al. *Gynecol. Oncol.* 58:230–239, 1995b; *Int. J. Gynecol. Cancer* 5:401–410, 1995c; *Am. J. Obst. Gynecol.* 174:633–639, 1996.

Golumbek et al. (1989) reported that mouse renal carcinoma cells inserted with a gene for IL-4 was strongly immunogeneic for systemic T cell immunity, and protected mice against a subsequent lethal challenge with unmodified, parental tumor cells. Cavallo et al. 1991 & 1992. Antitumor immunity is intensified by a cancer vaccine that produces both GM-CSF and IL-4. Wakimoto et al. (1996) *Cancer Res.* 56:1828–33. The cytokine or cytokine combination may recruit or stimulate cells of the immune system, and thereby overcome the normal barrier to immunity. Certain cytokines also affect the expression of major histocompatibility molecules and intercellular adhesion molecules by cancer cells (Santin et al. 1995a, *Int. J. Cancer* 65:688–694; Santin (1996) *Am. J. Obst. Gynecol*), potentially improving immunogenicity.

The experiments with cytokine-secreting histocompatible tumor cells have been done chiefly in genetically restricted animal models, which are not directly equivalent to a heterogeneous human patent population. Colombo et al. (1995) *Cancer Immunol. Immunother.* 41:265–270. Not all cancer types are responsive to the same cytokines. There are concerns about injecting human patients with replication-competent tumor cells, particularly after genetic alteration. In addition, there is usually not enough time to genetically alter and grow up sufficient cells of the patient to be treated for use in a vaccine.

Blumbach (WO 96/05866) has suggested vaccines of live tumor cells transduced with: a) a gene coding for an immunostimulatory protein; b) a cytokine; and c) a thymidine kinase gene. The composition is provided as live cells which can grow in vivo and stimulate a response, and then be selectively killed via the thymidine kinase. The possibility of escape mutants is likely to be a subject of regulatory concern for this approach in human therapy. Golumbek et al. (1992) *J. Immunother.* 12:224–230 have shown that proliferating tumor cells with suicide genes can also survive toxin treatment when they exit the cell cycle temporarily or are sequestered pharmacologically.

As an alternative, Cohen (WO 95/31107) suggested that neoplastic disease can be treated with a cellular immunogen comprising allogeneic cells genetically altered to express one or more cytokines, and also to express tumor-associated antigens encoded by autologous genomic tumor DNA. In this approach, an allogeneic cell (exemplified as a mouse LM cell) is genetically altered to express: a) a cytokine; and b) a tumor-associated antigen autologous to the subject to be treated. Accordingly, the vaccine need not comprise live tumor cells.

However, application of the Cohen invention to human subjects would require prior knowledge for each patient of a particular tumor-associated antigens expressed by the particular tumor. Many human cancers of widespread clinical interest do not have reliable commonly-shared markers. Once a relevant marker is identified for a particular patient, a cell line must be engineered accordingly, and cultured to the required density prior to treatment. Thus, each patient would become their own research and development project. Since the immune response would be focused only at the particular tumor-associated antigen used, it may be less effective than one directed against the spectrum of antigen expressed by a complete tumor cell. Furthermore, the vaccine comprises a live genetically altered cell line, raising the concerns outlined earlier. Cohen demonstrated only a modest improvement in survival in the animal studies, and failed to provide any evidence that his formulation would be effective in human cancer patients.

A suitable strategy for a human anti-tumor cellular vaccine has to contend with the following problems: a) heterogeneity amongst tumors (even tumors of the same type) in the display of tumor-associated antigens; b) heterogeneity in the immune response between individuals with regards to both antigens and cytokines; c) ethical and regulatory concerns about compositions that may be used in humans; and d) lack of development time in most clinical settings, limiting the ability to engineer new cell lines or otherwise tailor the vaccine to each patient.

SUMMARY OF THE INVENTION

This invention provides compositions and methods for eliciting an anti-tumor immune response in a human patient in need thereof The compositions of the invention are cell mixtures in physiologically compatible excipient, and are referred to herein as a vaccine or an immunogenic composition. They may be administered to patients either to treat or palliate a clinically detectable tumor, or for prophylaxis, particularly after surgical debulking, chemotherapy or radiation therapy of a previously detectable tumor. The compositions are typically administered at a location distant from the original tumor, with the objective of stimulating a systemic reactivity against the primary tumor and metastases. The reactivity may in turn eradicate or slow the development of tumor cells, either at the primary site, within metastases (if there are any), or both.

Minimally, the vaccines of this invention comprise two components. The first is a source of tumor antigen, preferably a plurality of antigens, which is associated with the cancer for which the patient is at risk. A convenient source of tumor-associated antigen is tumor cells previously obtained from the patient, such as during surgical resection. The second component is a stimulated lymphocyte population that can participate in stimulation of the patient's immune system to produce an anti-tumor response. In particular, the stimulated lymphocyte population comprises lymphocytes that are allogeneic to the patient. They are preferably pre-activated by coculturing ex vivo with stimulator cells such as leukocytes obtained from the patient or from a second third-party donor allogeneic to the donor contributing the reponder cells. Included in the invention are compositions comprising a plurality of stimulator or responder cells, or both, wherein the stimulator cells are capable of alloactivating the responder cells in culture.

Embodiments of the invention include compositions for treatment of cancer. One embodiment is a cellular vaccine suitable for administration to a human or other subject being treated, comprising an effective combination of the following components in a pharmacologically or physiologically compatible excipient: a) leukocytes from the human or from a third-party donor; b) lymphocytes allogeneic to the leukocytes, and preferably alloactivated against them; and c) an inactivated tumor cell population, consisting either of primary tumor cells obtained from the human, the progeny of such cells line cells, or a combination thereof. The first ingredient is optional where the allogeneic lymphocytes are otherwise stimulated prior to inclusion in the mixture. The inactivated tumor cell may be substituted by an alternative source of tumor-associated antigen, such as a tumor cell homogenate, detergent lysate, or a purified derivative thereof, such as an isolated protein.

The inactivated tumor cell population preferably consists essentially of primary tumor cells dispersed from a solid tumor resected from said human, and may be selected from the group consisting of glioma cells, glioblastoma cells, gliosarcoma cells, astrocytoma cells, and ovarian cancer cells. In other embodiments, non-solid tumors may be used, including but not limited to leukemias and lymphomas.

The allogeneic lymphocytes are typically isolated from peripheral blood of a suitable donor, and may optionally be genetically altered to express a cytokine at an elevated level, particularly IL-2, IL-4, GM-CSF, TNF-α or M-CSF, or any combination thereof. In a preferred embodiment, the leukocytes and lymphocytes are cocultured for a duration and under conditions sufficient for allogeneic stimulation or proliferation of the lymphocytes, prior to combination with said tumor cell population.

The invention also embodies the vaccines and immunogenic compositions of this invention in unit dosage or kit form. Also embodied are methods for producing any of the compositions of this invention by preparing or mixing the various components of the compositions, including coculturing leukocytes from a subject to be treated with allogeneic lymphocytes and/or combining stimulated allogeneic lymphocytes with primary tumor cells, progeny, or tumor antigen from the subject.

Also embodied are methods for inducing, boosting, or otherwise stimulating an anti-tumor immunological response, especially a cellular response, or for treating a neoplastic disease such as cancer, comprising administering any one of the compositions or vaccines of this invention. Further embodiments are methods for inducing, boosting, or otherwise stimulating an anti-tumor immunological response or treating a neuroplastic disease in a human in need of such treatment, comprising the steps of: a) mixing together in vitro a tumor associated antigen (particularly a tumor cell population) with a second cell population comprising stimulated lymphocytes allogeneic to the human; and b) administering an immunogenic amount of the cell mixture to the human.

An immunological response stimulated by one of the embodied methods may be a primary response, or a secondary response, and the human may optionally have been previously treated by administration of allogeneic lymphocytes into a solid tumor in the human or into a cavity in the human formed by removal of a solid tumor or a portion thereof. Preferably, the tumor cell population comprises primary tumor cells obtained from said human, or a tumor cell line derived from primary tumor cells obtained from said human, and is inactivated. In particular embodiments, the second cell population also comprises leukocytes from said human, which are preferably inactivated, and typically isolated from peripheral blood. Preferably, the leukocytes and lymphocytes are cocultured before adding to the tumor cells, for a duration and under conditions sufficient for allogeneic stimulation of the lymphocytes, or for proliferation of the lymphocytes, prior to combination with said tumor cell population. In particular embodiments, lymphocytes from the donor alternatively or in addition have been genetically altered to express a cytokine at an elevated level.

DETAILED DESCRIPTION

Figure 1A:
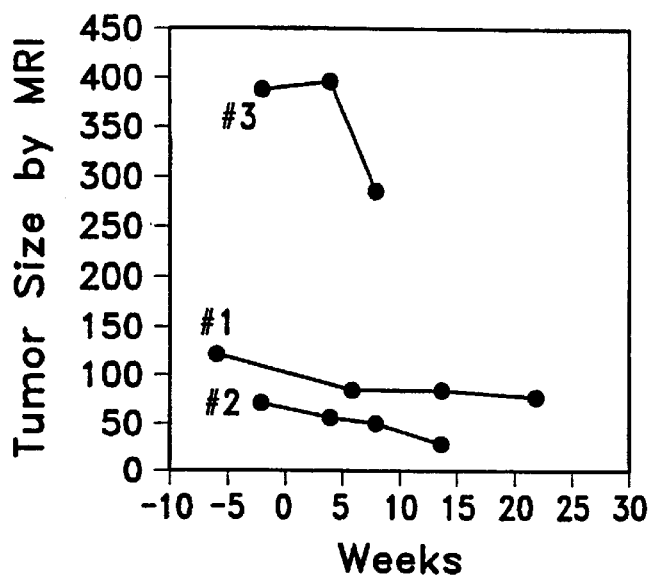
FIG. 1 is a three-panel graph showing relative tumor size measured by magnetic resonance imaging (MRI) in nine different patents at various times after intra-tumor implantation with 2, 4, or 6×10$^9$ cells (panels A, B, and C, respectively). The implant cells were obtained from a mixed lymphocyte culture of autologous and allogeneic leukocytes. Downward sloping lines are indicative of progressive reduction in tumor mass, attributed in part to a local immunological reaction resulting from the implant.

A central feature of the cellular vaccines of this invention is the use of multiple components that act in concert once inside the host to produce the desired effect. In other words, the strategy is more than just an adoptive immune transfer. One component of the vaccine is tumor antigen, preferably provided in the form of a cancer cell that expresses multiple tumor-associated antigens shared by the tumor of the patient to be treated. Previously established tumor cell lines may be used for this purpose, but it is particularly convenient to use cells obtained from the patient to be treated, either by surgical resection, biopsy, blood sampling, or other suitable technique. The other component is a mixture of cells including lymphocytes that are activated (or capable of being activated), and as a result, are capable of stimulating an enhanced immune response in the host. In certain preferred embodiments, the cell mixture is a mixed lymphocyte culture of allogeneic cells stimulated using cells obtained from the subject to be treated.

The strategy is a significant departure from previous approaches to cancer immunotherapy in humans. Stimulated lymphocytes have been used in experimental human therapy, but as part of adoptive therapy—the lymphocytes were originally obtained from the subject or a closely matched donor. In this invention, the stimulated lymphocytes are allogeneic to the subject. The stimulated lymphocytes provide a potent immunostimulation that elicits a response against simultaneously injected tumor associated antigen. As a result, a cellular immune response emerges that is specific for the tumor, and much stronger than can be achieved by simply administering the patent's tumor cells, or a derivative thereof.

The present invention was developed in conjunction with the observation that mixed lymphocytes implanted directly into a tumor bed limits or even reverses tumor growth. These experiments and the observations obtained therefrom are described in Example 1 below, and in commonly owned copending U.S. patent application Ser. No. 08/616,880, a continuation-in-part of Ser. No. 08/406,388 both of which are hereby incorporated herein by reference. The effect on tumor mass appears at least in part to be due to an active immunological reaction of host origin. In one patient, there was no evidence of residual allogeneic lymphocytes, even though there was histological evidence for extensive tumor necrosis. In addition, the effect appears to be long-lasting. Some patients given a single implant experienced a resolution in their condition that lasted for years. It was hypothesized that increased expression of transplantation antigens stimulated by allogeneic lymphocytes in the implant resulted in the massive recruitment of lymphoid cells near the tumor site. Either local graft-vs-tumor, graft-vs-host, host-vs-graft, or some combination of reactions of this kind were generated, and an immunological window opened for otherwise poorly immunogenic tumor antigens to initiate a cell mediated anti-tumor immune response.

An animal model has been developed for the implant protocol and a different type of cancer. As a model of metastatic cancer, the MADB $10^6$ $L^{-1}$ breast carcinoma cell line was used to instill primary tumors in the median hepatic lobe of Fisher 344 rats. Once tumors were well established, they were implanted with syngeneic stimulator lymphocytes and allogeneic responder lymphocytes precultured at a 1:1 ratio. The treated animals survived an average of almost twice as long as those given live tumor cells but not the implant. Long-term survivors were immune to rechallenge with normally fatal doses of parental breast cancer cells. Preculturing the mixed lymphocytes together was found to be important in obtaining the full effect (see Example 3, infra).

The combined results of these studies inspired the following conclusions: a) the mixed lymphocyte implant strategy is effective in improving survival in at least two different cancers (glioma, and the metastatic breast cancer model) and at least two different locations (the brain and the liver); b) survivors are resistant to rechallenge with parental tumor cells; and c) the effect may be mediated through immune activation of host anti-tumor immunity.

A particular glioblastoma patient treated with two successive implants did not respond adequately, and the implants were surgically removed. The patient was then treated with cryopreserved tumor cells recovered from the surgical procedure, mixed with yet another prepared culture of allogeneic and autologous lymphocytes. The mixture was administered not into the tumor bed, but at a subcutaneous site distant from the tumor (Examples 4 and 8). This experimental procedure worked surprisingly well in generating a systemic anti-tumor response. Even though this patient has no intratumor implant, she is responding as well as if she had. The conclusion is that distal administration of autologous tumor cells plus mixed lymphocytes is an effective cancer treatment method, probably due to a potent ability to increase immunogenicity of the tumor.

A hallmark of the cellular vaccines of the present invention is that the effect is substantially greater than that obtained using tumor cells alone, or tumor cells mixed with previously used adjuvants or cofactors. Interaction between the tumor cells and the stimulated lymphocytes of the vaccines is probably complex. While not wishing to be bound by any one theory, it seems possible that the tumor cell (or a tumor-associated antigen) is in effect a bystander in an immunological reaction generated in the host stimulated by the activated lymphocytes. The activated lymphocytes may participate in one or more of the following ways. First, they likely provide cytokines which are effective in recruitment, activation, or stimulating the interaction of host immune cells. The cytokine mixture produced is superior to a cytokine provided in isolated form or via a transduced cell, in part, because it is a cocktail of factors. Individual cytokines in the cocktail may work in concert or even synergistically to stimulate a variety of activities that are beyond what can be stimulated in a reliable fashion by a single cytokine. The cocktail may also comprise cytokines which have not yet been identified or isolated. Second, the activated lymphocytes may also play a direct role in tumor antigen presentation. Third, activated lymphocytes (particularly allogeneic lymphocytes) may play a contact role in stimulating immune cells of the host, during which the tumor antigen may participate as a bystander.

An immunological response resulting from administration of the vaccine may comprise both humoral and cellular components, but a cellular response is especially preferred. Cellular immunity (either cytotoxic lymphocytes, or helper-inducer cells recruiting other effector mechanisms) are believed to be important in providing a specific effect against the cells of the target neoplasm. The presence of an immunological response may be monitored by standard immunological techniques. However, in human therapy, a primary objective is an improvement in the clinical condition of the patient. Clinical outcome is therefore a superior assay for the effectiveness of the compositions and methods of this invention when directed towards cancer treatment.

The present invention is superior to strategies used or suggested previously. Advantages of the vaccine compositions of this invention include the following:

The vaccines improve the clinical condition or prognosis of human cancer patients. This is true even though tumor cells residing in cancer patients are apparently poorly immunogenic on their own.

Although the response is presumably mediated by a tumor-associated antigen, there is no need to confirm the presence of any particular antigen on the tumor of a treated subject. Use of patent's own tumor cells ensures a spectrum of relevant antigens.

There is no need to genetically alter patients' cells, or use patients' DNA to genetically alter cells of the vaccine. In fact, genetically altered cells are not required to obtain a response (although they may be included in particular embodiments of the invention, as described below).

The strategy is aimed at generating a systemic immune response, and may therefore be effective not only against the primary tumor, but also against metastatic cells sharing tumor antigen with the primary tumor.

With the possible exception of the initial sampling of the tumor cells, the protocol may be performed with minimally invasive procedures. The vaccine compositions are preferably administered at a site distant from the tumor. Subcutaneous routes of administration are preferred.

The effect is long-lived, persisting at least about two months. Since the vaccination procedure is designed to stimulate the host's immune system, it should require at most occasional supplementation. This is a considerable advance over adoptive transfer methods.

A further description of preferred methods to prepare and use the vaccine compositions of this invention are provided in the sections that follow.

Definitions

The terms "vaccine", "immunogen", or "immunogenic composition" are used herein to refer to a compound or composition, as appropriate, that is capable of conferring a degree of specific immunity when administered to a human or animal subject. As used in this disclosure, a "cellular vaccine" or "cellular immunogen" refers to a composition comprising at least one cell population, which is optionally inactivated, as an active ingredient. The vaccines, immunogens, and immunogenic compositions of this invention are active vaccines, which means that they are capable of stimulating a specific immunological response (such as an anti-tumor antigen or anti-cancer cell response) mediated at least in part by the immune system of the host. The immunological response may comprise antibodies, immunoreactive cells (such as helper/inducer or cytotoxic cells), or any combination thereof, and is preferably directed towards an antigen that is present on a tumor towards which the treatment is directed. The response may be elicited or restimulated in a subject by administration of either single or multiple doses. Nothing further is required of a composition in order for it to qualify as a vaccine, unless otherwise specified.

A compound or composition is "immunogenic" if it is capable of either: a) generating an immune response against an antigen (such as a tumor antigen) in a naive individual; or b) reconstituting, boosting, or maintaining an immune response in an individual beyond what would occur if the compound or composition was not administered. A composition is immunogenic if it is capable of attaining either of these criteria when administered in single or multiple doses.

"Stimulating" an immune or immunological response refers to administration of a compound or composition that initiates, boosts, or maintains the capacity for the host's immune system to react to a target substance, such as a foreign molecule, an allogeneic cell, or a tumor cell, at a level higher than would otherwise occur. Stimulating a "primary" immune response refers herein to eliciting specific immune reactivity in a subject in which previous reactivity was not detected; for example, due to lack of exposure to the target antigen, refractoriness to the target, or immune suppression. Stimulating a "secondary" response refers to the reinitiation, boosting, or maintenance of reactivity in a subject in which previous reactivity was detected; for example, due to natural immunity, spontaneous immunization, or treatment using one or several compositions or procedures.

A "cell line" or "cell culture" denotes higher eukaryotic cells grown or maintained in vitro. It is understood that the descendants of a cell may not be completely identical (either morphologically, genotypically, or phenotypically) to the parent cell.

"Inactivation" of a cell is used herein to indicate that the cell has been rendered incapable of cell division to form progeny. The cell may nonetheless be capable of response to stimulus, or biosynthesis and/or secretion of cell products such as cytokines. Methods of inactivation are known in the art. Preferred methods of inactivation are treatment with toxins such as mitomycin C, or irradiation. Cells that have been fixed or permeabilized and are incapable of division are also examples of inactivated cells.

"Mixed lymphocyte reaction", "mixed lymphocyte culture", "MLR", and "MLC" are used interchangeably to refer to a mixture comprising a minimum of two different cell populations that are allotypically different. At least one of the allotypically different cells is a lymphocyte. The cells are cultured together for a time and under suitable conditions to result in the stimulation of the lymphocytes. A frequent objective of an MLC is to provide allogeneic stimulation such as may initiate proliferation of the lymphocytes; but unless indicated, proliferation during the culture is not required. In the proper context, these terms may alternatively refer to a mixture of cells derived from such a culture. When cells from an MLC are administered as a bolus to a human, especially in a tumor bed, it is referred to as a "cytoimplant".

"Genetic alteration" refers to a process wherein a genetic element is introduced into a cell other than by mitosis or meiosis. The element may be heterologous to the cell, or it may be an additional copy or improved version of an element already present in the cell. Genetic alteration may be effected, for example, by transducing a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. It is preferable that the genetic alteration is inheritable by progeny of the cell, but this is not generally required for the practice of this invention, particularly when altered cells are used in a pharmaceutical composition without further proliferation.

The terms "tumor cell" or "cancer cell", used either in the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells.

The term "tumor-associated antigen" or "TAA" is used herein to refer to a molecule or complex which is expressed at a higher frequency or density by tumor cells than by non-tumor cells of the same tissue type. Tumor-associated antigens may be antigens not normally expressed by the host; they may be mutated, truncated, misfolded, or otherwise abnormal manifestations of molecules normally expressed by the host; they may be identical to molecules normally expressed but expressed at abnormally high levels; or they may be expressed in a context or milieu that is abnormal. Tumor-associated antigens may be, for example, proteins or protein fragments, complex carbohydrates, gangliosides, haptens, nucleic acids, or any combination of these or other biological molecules. Knowledge of the existence or characteristics of a particular tumor-associated antigen is not necessary for the practice of the invention.

As used herein, "treatment" refers to clinical intervention in an attempt to alter the natural course of the individual or cell being treated, and may be performed either for prophylaxis or during the course of clinical pathology. Desirable effects include preventing occurrence or recurrence of disease, alleviation of symptoms, diminishment of any direct or indirect pathological consequences of the disease, preventing metastasis, lowering the rate of disease progression, amelioration or palliation of the disease state, and remission or improved prognosis.

The "pathology" associated with a disease condition is anything that compromises the well-being, normal physiology, or quality of life of the affected individual. This may involve (but is not limited to) destructive invasion of affected tissues into previously unaffected areas, growth at the expense of normal tissue function, irregular or suppressed biological activity, aggravation or suppression of an inflammatory or immunological response, increased susceptibility to other pathogenic organisms or agents, and undesirable clinical symptoms such as pain, fever, nausea, fatigue, mood alterations, and such other features as may be determined by an attending physician.

An "effective amount" is an amount sufficient to effect a beneficial or desired clinical result, particularly the generation of an immune response, or noticeable improvement in clinical condition. An immunogenic amount is an amount sufficient in the subject group being treated (either diseased or not) sufficient to elicit an immunological response, which may comprise either a humoral response, a cellular response, or both. In terms of clinical response for subjects bearing a neoplastic disease, an effective amount is amount sufficient to palliate, ameliorate, stabilize, reverse or slow progression of the disease, or otherwise reduce pathological consequences of the disease. An effective amount may be given in single or divided doses. Preferred quantities and cell ratios for use in an effective amount are given elsewhere in this disclosure.

An "individual" or "subject" is a vertebrate, preferably a mammal, more preferably a human. Non-human mammals include, but are not limited to, farm animals, sport animals, and pets.

General Techniques

The practice of the present invention will employ, unless otherwise indicated, conventional techniques of molecular biology, microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); "Current Protocols in Immunology" (J. E. Coligan et al., eds., 1991). See also Gately et al., Lee et al., and Zarling et al. (infra) for examples of techniques in mixed lymphocyte cultures.

General procedures for the preparation and administration of pharmaceutical compositions are outlined in *Remington's Pharmaceutical Sciences* 18*th Edition* (1990), E. W. Martin ed., Mack Publishing Co., PA.

There are a number of animal models for cancer that can be used to test and adjust the compositions and methods of this invention. Certain models involve injecting in-bred animals with established syngeneic tumor lines. The tumors can be co-injected with a potentially therapeutic composition, allowed to establish before therapy is commenced, or administered as a challenge at some time following vaccination of a naive animal. Illustrations are provided in the Example section. Also useful are chimeric animal models, described in U.S. Pat. Nos. 5,663,481, 5,602,305 and 5,476,993; EP application 379,554; and International application WO 91/01760.

All patents, patent applications, articles and publications mentioned herein, both supra and infra, are hereby incorporated herein by reference.

Preparation of Cellular Vaccines

The cellular vaccines of this invention are typically assembled by preparing each cell population or equivalent thereof in an appropriate fashion, combining the components, and optionally coculturing or storing cell mixtures before administration to a subject.

Tumor-associated Antigen

The source of tumor-associated antigen is most usually a tumor cell or cell line that is close in phenotype to that for which the patient is being treated. Tumors from the same tissue type and with similar histological characteristics tend to share tumor-associated antigens. While the complete spectrum of antigens may vary between individual tumors, there is a substantial probability that at least one will be shared. Preferably, the tumor cells are histocompatible with the subject to be treated.

Generally, when it is possible to obtain tumor cells of patient origin, these cells are preferred as more likely to bear a full complement of relevant tumor-associated antigens. Circulating tumors such as leukemias and lymphomas may be readily sampled from peripheral blood. Otherwise, tumor cells are generally sampled by a surgical procedure, including but not limited to biopsy, or surgical resection or debulking. Tumor cells may also be collected from metastatic sites. Solid tumors can be dissociated into separate cells by physical manipulation optionally combined with enzymatic treatment with such proteases as collagenase and the like. The cells are then transferred into fresh physiological medium. Cells may be stored until further use, for example, by freezing in liquid $N_2$. Optionally, and especially when the original tumor mass is small, it is permissible to expand the tumor cell population to ensure an adequate supply. Cells are cultured in a growth medium suitable for propagation, optionally supplemented with growth factors. Preferably, a stable cell population comprising features of the tumor cells is obtained without further transformation, although this is permissible where required. The cell population may optionally be cloned to enhance its stability or refine its characteristics, although this is generally not necessary. Conditions for reliably establishing short-term cultures and obtaining at least $10^8$ cells from a variety of tumor types is described by Dillman et al. (1993) *J. Immunother.* 14:65–69. If possible, the original tumor cell preparation is used without proliferation, since it is possible that a critical tumor antigen will be lost through the proliferative process.

Cancer cells or cell lines obtained as described may be combined directly with the other components of the vaccine. However, it is preferable to inactivate the cancer cells to prevent further proliferation once administered to the subject. Any physical, chemical, or biological means of inactivation may be used, including but not limited to irradiation (preferably with at least about 5,000 cGy, more preferably at least about 10,000 cGy, more preferably at least about 20,000 cGy); or treatment with mitomycin-C (preferably at least 10 µg/mL; more preferably at least about 50 µg/mL).

Cancer cells for use as a tumor antigen source can alternatively be fixed with such agents as glutaraldehyde, paraformaldehyde, or formalin. They may also be solubilized in an ionic or non-ionic detergent, such as deoxycholate or octyl glucoside, or lysed, for example, using vaccinia virus. If desired, solubilized cell suspensions may be clarified or subject to any of a number of standard biochemical separation procedures to enrich or isolate particular tumor-associated antigens. Before combination with other components of the vaccine, the preparation is depleted of the agent used to treat it; for example, by centrifuging and washing the fixed cells, or dialysis of the solubilized suspension. Such treatment of the tumor cell population, particularly beyond inactivation, may be viewed as optional and unnecessary for the practice of the embodiments of the invention, unless specifically required.

Allogeneic Cells

The cellular vaccines of this invention also comprise a second cell population, of which at least a portion are cells allogeneic to the subject to be treated and capable of specifically reacting to an allogeneic stimulus. This generally means lymphocyte cells or cells of the lymphocyte lineage, particularly T cells. Lymphocytes expressing CD4 antigen (CD4+ cells), and cells expressing CD8 antigen (CD8+ cells) are both included in the definition of T lymphocytes, and either or both may be included in the vaccine. Preferably, the allogeneic cells in the second cell population are at least 10% CD4+ cells or 10% helper/inducer cells; more preferably they are at least about 20% of CD4+ or helper/inducer cells; even more preferably the portion is at least about 30%; still more preferably the portion is at least about 50%. CD4+ cells may be conveniently quantified with commercially available specific antibody such as OKT4 in conjunction with fluorescence-activated counting.

Cells are generally described as allogeneic if they bear a phenotypic difference sufficient to stimulate an alloreaction. In the context of this disclosure, use of the term "allogeneic" is restricted to a difference in phenotype of major histocompatibility complex (MHC) antigens. Any qualitative difference in the identity of MHC allotypes between cells of the same species means they are allogeneic cells. In humans, differences at any of the HLA-A, B, C, D, DP, DQ, and DR loci constitute allotypic differences relevant for this invention. Identity of HLA-A, B, C, DP, DQ, and DR are typically determined using allotype-specific antibodies in a cytotoxicity or immunofluorescence technique. Preferred allotypic differences for the purposes of the present invention relate to HLA class II antigens. Comparing the class II antigens of the DP, DQ, and DR loci between the putative allogeneic cells and cells of the subject to be treated, preferably at least 1, and increasingly more preferably 2, 3, 4, 5, or even 6 loci are different between allogeneic cells. Class II antigens may also be determined at the D locus by mixed lymphocyte reaction using typed cells. Donors of allogeneic cells are generally unrelated to the subject being treated, to maximize the number of MHC mismatches The number of class II region mismatches is related but secondary to a functional determination of allogenicity. Allogeneic cells are particularly suitable for use in the present invention if they demonstrate a strong proliferative response in a one-way MLR, using inactivated mononuclear cells of the subject to be treated as stimulator cells. Donors of cells known to produce a particularly strong response, particularly to stimulator cells of the same genotype as the subject, are especially suitable. A panel of different allogeneic cells can be tested against the patient cells to determine those that elicit the strongest response.

The allogeneic cell population is not necessarily restricted to those obtained from a single donor. Two, three, or a higher plurality donors may optionally be used to facilitate collection of the allogeneic cells, to increase stimulation of the allogeneic cells, to minimize the elicitation of an anti-allotype response, or to otherwise enhance the efficacy of the cellular vaccine.

Allogeneic cells are preferably activated or stimulated before administration to the subject, or are capable of activation or stimulation once administered. "Activation" in this context means induced to proliferate. Proliferation may be measured by cell counting, or by a standard [$^3$H]-thymidine uptake assay during the last ~18 hours of culture. Stimulation of the cells with a mitogen such as PHA shows the maximum proliferation, and culturing without the inducing agent cells measures base line proliferation. Substantially proliferating cells will show uptake substantially above base line levels.

"Stimulation" in this context means induced by an external agent to undergo a metabolic alteration, particularly an increase in the synthesis and/or secretion of biologically relevant molecules such as cytokines or other soluble mediators, a morphological change from a quiescent lymphocyte to a lymphoblast, or an increase in biological reactivity in the cell including but not limited to an increase in endocytosis, exocytosis, phagocytosis, or intracellular transport and processing of molecules from the external environment. A number of biological assays are relevant for the measurement of activation and stimulation, including proliferation and cytotoxicity assays, histological examination, measurement of the density of cell-surface markers, measurement of mediators (particularly cytokines) synthesized and/or excreted by the cell, or an increased ability to recruit effector cells such as neutrophils, basophils, mast cells, monocytes, macrophages, eosinophils, and other lymphocytes. Stimulation takes place when the assay reveals a change in the feature being measured upon induction that exceeds those observed in the absence of induction. Particularly relevant forms of stimulation are those correlated with increased frequency of participation of cells bearing such features in an immunological response. Such features include blastogenesis, proliferation or cytotoxicity in response to specific antigen, and increased secretion of the mediators IL-2, IL-4, IL-6, TNF-α, IFN-γ, G-CSF, M-CSF, or GM-CSF. Certain assays for measuring stimulation are provided in Example 5.

Lymphocytes may be collected for use with this invention from any suitable tissue source, but are most conveniently obtained from the blood of an allogeneic donor. Donors are preferably prescreened to identify those with sufficient leukocyte count, and exclude those with neoplastic conditions or transmissible infections. Collection may be performed by whole blood donation followed by separation of blood cell populations, or more conveniently by leukapheresis. Sufficient blood is processed to obtain about 100–500 mL leukapheresis suspension, preferably at least about 200 mL. Blood is collected in anticoagulant, such as citrate or EDTA. For example, leukapheresis may be performed using a Cobe 2997 (COBE SPECTRA®, Lakewood, Colo.); Fenwall CS 300 (Fenwall, Deerfield Ill.); or Haemonetrics (Braintree Mass.) blood cell separator. Flow rates of ~40–50 mL/min for 2–4 h yield ~200–250 mL leukapheresis suspension having <1 mL red cells, with variations between individual donors and the equipment used.

Lymphocytes prepared by any suitable method are generally washed to remove platelets, and resuspended in a suitable medium, such as AIM V supplemented with 2% inactivated fetal calf serum. If desired, cells may be further separated into subpopulations in order to enrich for lymphocytes, particularly T cells. Both positive and negative selection methods may be used. Suitable procedures include centrifugation over a suitable medium such as FICOLL™ or HISTOPAQUE®, passage over a nylon-wool column, affinity separation methods such as panning, or sorting in a fluorescent cell sorter using an antibody against a relevant cell-surface marker. For the sake of convenience, it may be preferable to decrease the number of manipulation steps. For example, better leukapheresis separation may obviate the need for subsequent separation on FICOLL™.

The allogeneic cells may be stimulated in any fashion that potentiates the immune response to relevant tumor-associated antigens. LAK cells and TIL cells are included in the definition of stimulated allogeneic cells. LAK and TIL cells may be generated and separated according to techniques known in the art; a chief difference for use in the present invention is that they be allogeneic to the intended recipient. This invention encompasses any means of activation or stimulation of the allogeneic cells, including but not limited to preculturing with cells of neither donor nor patient origin, preculturing with live (non-inactivated) tumor cells, preculturing with feeder cells of donor origin, preculturing with isolated or recombinant cytokines or mixtures thereof, preculturing with mitogens such as ConA, or any combination of the techniques listed. Methods for stimulating immune cells and assays for determining stimulation can be found inter alia in U.S. Pat. No. 5,569,585.

A particularly preferred method of stimulation is by mixed lymphocyte culture, as is known in the art and further described herein.

Stimulator Cells

A preferred method for stimulating the allogeneic lymphocytes is to combine them with cells which are capable of providing suitable stimulation. Such cells are referred to herein as "stimulator" cells. The allogeneic lymphocytes, when stimulated in this way are referred to as "responder" cells. Preferred stimulator cells are cells which are allogeneic to the responder cells.

In certain embodiments of this invention, the source of stimulator cells is an individual genetically similar to the subject to be treated; even more preferably, the stimulator cells are from an individual who is similar or identical to the subject in terms of MHC antigens, even more preferably, the cells are autologous to the subject. In some cases, the subject may have had a previous immune response against tumor-associated antigen, due to stimulation by the tumor or prior treatment.

In other embodiments of this invention, the stimulator cells are not from the subject to be treated, but from another donor or plurality of donors. The advantage of using subject's cells is that the responders will continue to receive stimulation from the subject's alloantigens after administration. However, use of third-party stimulators has its own set of advantages. For example, batches of stimulated cells may be prepared for use in several different patients. By way of illustration, leukapheresis cells from several different donors other than the subjects to be treated are pooled and cultured together under conditions sufficient for stimulation. Aliquots of the cultured cells are then combined from tumor cells from each individual patient in order to form a cellular vaccine tailored to each patient's tumor-associated antigens.

In further embodiments of the invention, a plurality of stimulator cells from different individuals is used, which may or may not include the subject to be treated.

Suitable cell types for use as stimulator cells are those that bear a high density of histocompatibility antigens, particularly class II antigens. Lymph node cells are suitable, but a more usual source is peripheral blood. Leukocytes or white cells may be collected from the circulation of the subject by leukapheresis; however, whole blood collections are more usual, and usually more convenient since the number of stimulator cells required is much lower than the number of responder cells. 200–400 mL of peripheral blood collected by vena puncture in a suitable anticoagulant typically provides sufficient cells to prepare the vaccine.

The separation procedures described above may generally be employed to rescue stimulator cells from the subject's whole blood sample. It is desirable to enrich for, or at least not to deplete cells expressing class II histocompatibility antigens from the population, such as B cells and monocytes. Extensive subfractionation of the cells is not usually required, and a simple peripheral blood mononuclear cell population (PBMC) is adequate for most purposes.

Mixed Lymphocyte Cultures

Donor allogeneic lymphocytes and stimulator cells, when used, may be combined just before administration to the patient, with the expectation that the allogeneic stimulation will take place in vivo. However, the data provided in Example 3 has shown that coculturing the two cells before administration enhances the effect of the composition.

This invention encompasses the use of two-way mixed lymphocyte cultures as a way to stimulate the allogeneic cells. However, when using the tumor patient's leukocytes as stimulator cells, one-way MLCs are preferred. To conduct a one-way MLC, the subject's stimulator cells are inactivated, for example, by treating ~$10^7$ cells/mL with 50 µg/mL mitomycin C, followed by washing.

Allogeneic lymphocytes are combined with stimulator cells in a suitable medium, generally supplemented with fetal calf serum or a substitute therefor, and optionally including other growth factors. The ratio of responder-:stimulator cells is preferably between about 100:1 to 1:10; more preferably about 50:1 to 1:1; still more preferably about 20:1 to 5:1, and even more preferably about 10:1. Where there are a plurality of stimulator or responder cells in a one-way MLC, the same approximate ratio of responders:stimulators is maintained. Thus, when using 2 inactivated stimulators, the ratio may be approximately 9:(1:1); when using 3 inactivated stimulators, the ratio may be approximately 8 :(1:1:1). Similarly, when using multiple responders, the ratio may be (5:5):1 or (3:3:3):1. If cultured together, the multiple responder composition becomes a multi-way MLC. One-way activation of multiple responders can be achieved by conducting a separate culture for each responder population at a 10:1 ratio, and then combining the alloactivated cells just before use.

Once combined in the desired ratio, the cells cultured at an appropriate density in a suitable atmosphere (such as 95% $O_2$, 5% $CO_2$ at about 37° C.). The culture period is preferably at least about 12 h, more preferably between about 24 h and 72 h. Additional stimulation may be obtained by culturing for 3–5 days, although this is generally not preferred, since cytokine levels are normally higher during the first 48 to 72 h of culture. The practitioner may determine whether conditions are sufficient for proliferation or stimulation of the responder cells by performing a bioassay for these properties as described earlier or in Example 5. In another method, levels of TNF-α, LT and/or IFN-γ are measured in the culture supernatant. Stimulation is indicated by levels of biological activity of TNF-α or LT at 50–150 U/mL, or 500–3500 pg/mL. Preferred cultures are those that show a level of activation ≧10% above unstimulated donor control value within the first 3 days of culture, as measured by the Tetrazolium Reduction Assay (XTT), or by Flow Cytometry (CD69 or intracellular esterase), or both.

The recitation within this disclosure of preferred cell sources, cell ratios, culture conditions, and other features, is intended as an aid to the practitioner and is not meant to limit the scope of the invention, unless explicitly required. No limitation is implied with respect to any of the individual parameters, since various other parameter combinations will generate a cell population with the desired functional effect.

The mixed lymphocyte culture is generally conducted with allogeneic responder cells and subject's stimulator cells prior to addition of the tumor cells. Usually, the stimulator cells, although derived from a cancer patient, are themselves non-cancerous. However, it is permissible for the tumor cells to be present during the MLC. On occasion, the stimulator cells and the tumor cells may be the same, such as in the treatment of a leukemia.

Optimizing the Functional Effect

Experience in animal model experiments shows that not all third-party donors provide the same degree of alloactivation, particularly when a different third-party donor is used as the stimulator cell.

To the extent that variability is donor-cell dependent, donors can be chosen according to experience, both in terms of the degree of alloactivation observed in culture, and the clinical result. Functional criteria indicating a particular level of activation, such as the Tetrazolium Reduction Assay (XTT), Flow Cytometry Assay, or the level of secretion of certain lymphokines determined by ELISA, may be sufficiently predictive of outcome, depending on clinical experience. Once successful donors are identified, they may be constituted in a panel of regular donors sourced by the service lab providing the immunogenic compositions.

To the extent that the variability depends on the match between donors and patient, several other selection criteria can also be used. Since the efficacy of certain donor-patient combinations may migrate according to histocompatibility, donors can be selected, if desired, on the basis of tissue match. Donors of particular human histocompatibility types can be tested for efficacy with particular tumors, if desired, using one of the chimeric animal models listed earlier.

A more immediate donor identification test can be conducted using PBLs from the patient and PBL from a selection of potential donors in an in vitro assay. One such assay is a reverse functional test. In this assay, patients cells are set up in a mixed lymphocyte culture using the responder, using the potential donor of the alloactivated cells as the inactivated stimulator.

Since the response is thought to involve cytokine secretion by the alloactivated cells, an alternative predictor may be a two-stage culture. In this approach, a responder:stimulator culture is set up using the same responder and stimulator cells being tested for use in the preparative culture. At 3 days, the culture is inactivated with mitomycin or sub-lethal irradiation, so that cells can still produce cytokines but not replicate. Leukocytes from the patient are then added, and their response is followed by a functional assay, cytokine secretion, or T cell proliferation. In a variation of this approach, inactivated tumor cells are also provided in the second stage of the culture, and read-out is determined at the end of the second stage by measuring cytolysis of $^5$Cr labeled tumor cells.

These assays are described for the benefit of the reader who may wish to optimize the compositions of this invention in various ways, particularly in setting up a donor panel enriched for high responders. It should be emphasized that the invention can be practiced without employing the additional refinements outlined in this section.

The degree of alloactivation or the potential therapeutic outcome can also be enhanced by employing one or more of the following strategies, where available and appropriate: a) using a plurality of donor cells as the responder or stimulator in the MLC; b) using cells from the patient to be treated as stimulator in the MLC; c) adding an H2 receptor antagonist to the culture medium of the MLC. A preferred H2 receptor antagonist is cimetidine, added to the culture medium at between 5 μg/mL and 100 μg/mL, typically 20 μg/mL. The benefits of using cimetidine or a plurality of donor cells are illustrated in Examples 6 and 7, respectively.

Genetically Altered Cells

The allogeneic cells used in the vaccine can be genetically altered in a fashion that potentiates the immune response to the vaccine. Particularly preferred are allogeneic cells genetically altered to express cytokines at elevated levels. It is recognized that lymphocytes, particularly those in an allogeneic mixture, may already produce detectable levels of certain cytokines. "Elevated levels" of expression occurring as a result of genetic alteration exceed levels observed in cells not genetically altered in the same way, but otherwise similar. Any cytokine may be used for this purpose, especially those that have the ability to recruit or stimulate cells of the lymphocyte or antigen-presentation lineage or otherwise participate in accentuating the immune response. Preferred cytokines include, but are not limited to, tumor necrosis factors, exemplified in TNF-α; interleukins, exemplified in IL-2, IL-4, IL-6, IL-7, and IL-1 0; interferons, exemplified in IFN-α and IFN-γ; hematopoetic factors; and colony stimulating factors, exemplified in GM-CSF and M-CSF.

Amongst the possible cytokines that can be used with this invention, GM-CSF is especially preferred because of its important role in the maturation and function of specialized antigen-presenting cells. This is believed to be important because many tumor cells, such as those of epithelial origin, do not express detectable MHC class II molecules. IL-4 is also especially preferred, as a pluripotent cytokine endowed of a broad range of stimulating activities on both B and T lymphocytes, as well as on hematopoietic cells. Its roles include the recruitment and activation of CD4+ antigen-presenting cells, as well as induction of cytotoxic T lymphocytes. TNF-α is a third cytokine which is especially preferred, in part because of its broad range of effects in the immune and inflammatory response.

The protein and DNA encoding sequences of human IL-4 and TNF-α are known, and vectors comprising encoding sequences are available. For the IL-4 sequences and vectors, see U.S. Pat. No. 5,017,691 and EP 230107. Genetically altered CHO cells are described in U.S. Pat. No. 5,034,133. The use of IL-4 (either as the isolated recombinant or in a genetically altered cell) in treating solid tumors are described in U.S. Pat. No. 5,382,427. TNF polypeptides, encoding sequences, vectors, and genetically altered host cells are described in U.S. Pat. No. 5,288,852, EP 155549, and U.S. Pat. No. b4,879,226. Variants of TNF, which may also be used in this invention, are described in U.S. Pat. No. 4,677,063. Compositions comprising TNF-α and interferon are taught in EP 131789. Synergism of TNF and IL-4 in the inhibition of cancer cell growth is described in WO 92/05805.

Genetic alteration may be effected by any method known in the art. Typically, an encoding sequence for the desired cytokine is operatively linked to a heterologous promoter that will be constitutively or inducibly active in the target cell, along with other controlling elements and a poly-A sequence necessary for transcription and translation of the protein. The expression cassette thus composed is introduced into the cell by any method known in the art, such as calcium-phosphate precipitation, insertion using cationic liposomes, or using a viral vector tropic for the cells. Methods of genetic alteration are described in the patent publications cited in the preceding paragraph. One preferred method of genetic alteration is the use of the LXSN retroviral vector comprising a suitable expression cassette, as illustrated in Example 2. Another preferred method is the use of adenovirus vectors (M. Graf et al. abstract 1994). Briefly, adenoviral recombinant expression vectors prepared by genetic engineering of commercially available plasmids such as those supplied by Microbix, Canada. Suitable infection conditions and multiplicities of infection (MOI) may be determined in preliminary experiments using a reporter gene such as β-galactosidase, and then used for cytokine transfer (Kammersheidt et al.). An advantage of using a viral vector is that the vector may first be replicated, and then an entire population of cells may be infected and altered. Accordingly, genetically altered cytokine secreting cells may be established as a cell line, or a fresh leukapheresis preparation is altered de novo just prior to use in a vaccine of this invention. In the latter instance, preparation of the vaccine would additionally comprise the step of infecting a population of cells allogeneic to the intended recipient with a viral vector comprising an encoding region for a particular cytokine of interest.

Genetic alteration of allogeneic lymphocytes may be conducted as an alternative to or in addition to coculturing with leukocytes from the subject to be treated. Conferring the ability to produce a suitable cytokine or mixture of cytokines may allow the allogeneic lymphocytes to be self-stimulating, obviating the requirement for coculturing with subject leukocytes. More frequently, the two effects will be complementary or even synergistic, and it may be preferable to do both. For example, lymphocytes altered to produce a principal cytokine are then cocultured with subject leukocytes which may then activate the production of other cytokines in lesser but important amounts.

Similar procedures may be used to genetically alter primary tumor cells or tumor cell lines for use in the vaccine compositions, so that they produce cytokines. Description of such altered tumor cells is provided in Example 2. In general, it is preferable to genetically alter the allogeneic lymphocytes rather than the tumor cells; in part, because the tumor cells are typically irradiated before administration to the subject. Nevertheless, altering tumor cells may confer certain advantages. In particular, tumor cells readily form stable cell lines. Such lines (particularly those bearing a spectrum of common tumor-associated antigens) can be used to create a standard cytokine-secreting cell line for use in vaccines for treating a plurality of subjects. As shown in Example 2, tumor lines can be created that continue to produce cytokine from the genetic alteration for some time after a dose of radiation that halts proliferation. For use in the present invention, lines with these properties are developed, and propagated or maintained in culture just until the assembly of the vaccine. The required number of tumor cells are irradiated at the correct dose and mixed with the allogeneic lymphocytes; meanwhile a reserve of live altered tumor cells is kept in reserve if needed for booster injections.

Assembly of the Vaccine

To maximize viability of the various cells in the population or maintain their intended function, it is generally preferable to assemble the vaccine close to the time of administration. Various cell populations may be collected in advance, and cultured or cryopreserved to the extent consistent with the cell type and function in the vaccine. Freshly obtained cells are preferred. Cells from the mixed lymphocyte culture, or the entire vaccine, may also be cryopreserved as a mixture. However, it is preferable to conduct the MLC and then add the tumor cells shortly before administration to the patient.

When the allogeneic cells are stimulated by an MLC, there will usually be three cell populations in the vaccine: subject tumor cells, stimulator cells, and allogeneic responder cells. The role of the stimulator cells is primarily to stimulate the allogeneic cells in vitro, and it may not be necessary to have them present in the final vaccine composition. Thus, they may optionally be removed, although this is not usually necessary.

It is important to remove any additional components used in preparing the cells, particularly in the MLR, which may have an unwanted effect in the subject. In particular, fetal calf serum, bovine albumin, or other biological supplements in the culture medium are typically removed so as to avoid an immunological side reaction against them. Typically, the cell components of the vaccine are washed, such as by repeated gentle centrifugation, into a suitable pharmacologically compatible excipient. Compatible excipients include isotonic saline, with or without a physiologically compatible buffer like phosphate or Hepes and nutrients such as dextrose, physiologically compatible ions, or amino acids, and various culture media suitable for use with lymphocyte populations, particularly those devoid of other immunogenic components. Carrying reagents, such as albumin and blood plasma fractions and nonactive thickening agents, may also be used. Non-active biological components, to the extent that they are present in the pharmacological preparation, are preferably derived from the same species as that to be treated, and are even more preferably obtained previously from the subject.

The vaccine compositions of this invention may optionally include additional active components working independently or in concert with the tumor associated antigen and activated allogeneic cells. Such optional components include but are not limited to isolated or recombinant cytokines, particularly those explicitly referred to in this disclosure, adjuvants, and other cell types.

A vaccine composition of this invention is deemed "suitable" for administration to a human if reasonable and acceptable standards have been taken to ensure that the vaccine itself will not confer additional major pathology on the recipient. Side effects such as local inflammation, induration, or pain, or a febrile response may be unavoidable and are generally acceptable if the treatment is otherwise successful in a substantial proportion of patients. However, the composition should be reasonably free of: a) unrelated and pathological infectious or chemical agents, particularly from the donor of the allogeneic lymphocytes; b) undesirable growths as may be generated or propagated in tissue culture, such as bacteria or bacterial toxins, mycobacteria, and viruses; c) unacceptable levels of oncogenic agents or aggressively growing cancer cells not originating from the subject being treated; and d) components liable to initiate or effect an undesirable immune reaction, particularly anaphylactic shock. Particular tests that can be used are listed in the example section of this disclosure.

The compositions of the present invention, and subcomponents thereof may be supplied in unit dosage or kit form. Kits of this invention may comprise various components of a cellular vaccine or pharmaceutical composition are provided in separate containers. The containers may separately contain cells or antigens such when mixed together constitute a vaccine of this invention in unit dosage or multiple dosage form. Preferred kits comprise in separate containers: stimulated lymphocytes allogeneic to said human, particularly cells obtained from a coculture of allogeneic lymphocytes and autologous leukocytes; and tumor-associated antigen from the human, particularly primary tumor cells from the human, or progeny thereof. Alternatively, the kits may comprise a cell mixture in one container and a pharmaceutical excipient in another container. A preferred kit in this category comprises in a first container: stimulated lymphocytes allogeneic to a subject to be treated, particularly cells from a mixed lymphocyte culture; and in a second container: a pharmaceutical excipient. The user can employ the excipient to prepare their own tumor cells from the subject; the cells then are combined with the stimulated allogeneic lymphocytes for administration to the subject. Packaged compositions and kits of this invention typically include instructions for storage, preparation and administration of the composition.

Use of Cellular Vaccines in Cancer Treatment

The compositions of this invention may be administered to subjects, especially but not limited to human subjects. They are particularly useful for eliciting an immune response against a tumor-associated antigen, or for treating cancer.

Objectives of Treatment

One purpose of administering the vaccine is to elicit an immune response. The immune response may include either humoral or cellular components, or both. Humoral immunity may be determined by a standard immunoassay for antibody levels in a serum sample from the treated individual.

Since cellular immunity is thought to play an important role in immune surveillance of cancer, generating a cellular immune response is frequently a particular objective of treatment. As used herein, a "cellular immune response" is a response that involves T cells, and can be observed in vitro or in vivo.

A general cellular immune response may be measured as the T cell proliferative activity in cells (particularly PBL) sampled from the subject after vaccine administration. Inactivated tumor cells, preferably derived from the subject, are used as stimulators A non-specific mitogen such as PHA serves as a positive control; incubation with an unrelated stimulator cell serves as a negative control. After incubation of the PBMCs with the stimulators for an appropriate period (typically 5 days), [$^3$H]thymidine incorporation is measured.

If desired, determination of which subset of T cells is proliferating can be performed using flow cytometry. T cell cytotoxicity (CTL) may also be measured. In this test, an enriched T cell population from the subject are used as effectors in a standard $^{51}$Cr release assay. Tumor cells are radiolabeled as targets with about 200 $\mu$Ci of Na$_2$$^{51}$CrO$_4$ for 60 minutes at 37° C., followed by washing. T cells and target cells (~1×10$^4$/well) are then combined at various effector-to-target ratios in 96-well, U-bottom plates. The plates are centrifuged at 100×g for 5 minutes to initiate cell contact, and are incubated for 4–16 hours at 37° C. with 5% CO$_2$. Release of $^{51}$Cr is determined in the supernatant, and compared with targets incubated in the absence of T cells (negative control) or with 0.1% TRITON™ X-100 (positive control).

Another purpose of administering the vaccine is for treatment of a neoplastic disease, particularly cancer. Beneficial effect of the vaccine will generally be at least in part immune mediated, although an immune response need not be positively demonstrated in order for the compositions and treatment methods to fall within the scope of this invention, unless otherwise required.

Suitable Subjects

The compositions of this invention may be used for administration to both human and non-human vertebrates. They provide advantages over previously available compositions particularly in outbred populations, and particularly in spontaneous tumors. Veterinary applications are contemplated within the scope of the invention.

Cellular vaccines have been tested in human subjects, and are especially suitable for human treatment. The vaccines may be given to any human subject with the discretion of the managing physician. Typically, the subject will either have cancer, or be at substantial risk of developing cancer.

Typical human subjects for therapy comprise two groups, which may be distinguished by clinical criteria. Patients with "advanced disease" or "high tumor burden" are those who bear a clinically measurable tumor. A clinically measurable tumor is one that can be detected on the basis of tumor mass (e.g., by palpation, MRI, CAT scan, X-ray, or radioscintigraphy; positive biochemical or histopathological markers on their own are insufficient to identify this population).

A vaccine composition embodied in this invention is administered to patients with advanced disease with the objective of palliating their condition. Ideally, reduction in tumor mass occurs as a result, but any clinical improvement constitutes a benefit. Clinical improvement includes decreased risk or rate of progression or reduction in pathological consequences of the tumor.

A second group of suitable subjects is known in the art as the "adjuvant group". These are individuals who have had a history of cancer, but have been responsive to another mode of therapy. The prior therapy may have included (but is not restricted to) surgical resection, radiotherapy, traditional chemotherapy, and other modes of immunotherapy. As a result, these individuals have no clinically measurable tumor by the definition given above. However, they are suspected of being at risk for recurrence or progression of the disease, either near the original tumor site, or by metastases. The adjuvant group may be further subdivided into high-risk and low-risk individuals. The subdivision is made on the basis of features observed before or after the initial treatment. These features are known in the clinical arts, and are suitably defined for each different cancer. Features typical of high risk subgroups are those in which the tumor has invaded neighboring tissues, or which show involvement of lymph nodes.

A vaccine composition embodied in this invention is administered to patients in the adjuvant group in order to elicit an anti-cancer response primarily as a prophylactic measure against recurrence. Ideally, the composition delays recurrence of the cancer, or more preferably, reduces the risk of recurrence (i.e., improves the cure rate). Such parameters may be determined in comparison with other patient populations and other modes of therapy.

Of course, crossovers between these two patient groups occur, and the vaccine compositions of this invention may be administered at any time that is appropriate. For example, therapy may be conducted before or during traditional therapy of a patient with high tumor burden, and continued after the tumor becomes clinically undetectable. Therapy may be continued in a patient who initially fell in the adjuvant group, but is showing signs of recurrence.

Examples of tumors that can be treated by the compositions and methods of this invention include the following: pancreatic tumors, such as pancreatic ductal adenocarinomas; lung tumors, such as small and large cell adenocarinomas, squamous cell carcinoma, and brionchoalveolar carcinoma; colon tumors, such as epithelial adenocarcinoma and their metastases; and liver tumors, such as hepatoma and cholangiocarcinoma. Also included are breast tumors, such as ductal and lobular adenocarcinoma; gynecologic tumors, such as squamous and adenocarcinoma of the uterine cervix, and uterine and ovarian epithelial adenocarcinoma; prostate tumors, such as prostatic adenocarcinoma; bladder tumors, such as transitional squamous cell carcinoma; tumors of the RES system, such as nodular or diffuse B or T cell lymphoma, plasmacytoma, and acute or chronic leukemia; skin tumors, such as malignant melanoma; and soft tissue tumors, such as soft tissue sarcoma and leiomyosarcoma. Of especial interest are brain tumors, such as astrocytoma, oligodendroglioma, ependymoma, medulloblastomas, and primitive neural ectodermal tumor. Included in this category are gliomas, glioblastomas, and gliosarcomas.

The immune status of the individual may be any of the following: The individual may be immunologically naive with respect to certain tumor-associated antigens present in the composition, in which case the compositions may be given to initiate or promote the maturation of an anti-tumor response. The individual may not currently be expressing anti-tumor immunity, but may have immunological memory, particularly T cell memory relating to a tumor-associated antigen comprised in the vaccine, in which case the compositions may be given to stimulate a memory response. The individual may also have active immunity (either humoral or cellular immunity, or both) to a tumor-associated antigen comprised in the vaccine, in which case the compositions may be given to maintain, boost, or maturate the response, or recruit other arms of the immune system. The subject should be at least partly immunocompetent, so as to minimize a graft versus host reaction of pathological scope. However, it is recognized that cancer patients often show a degree of immunosuppression, and this does not necessarily prevent the use of the compositions of the invention, as long as the compositions may be given safely and effectively. Immunocompetence in the subject may be of host origin, or may be provided by way of a concurrent adoptive transfer treatment.

Modes of Administration and Dose

The compositions of this invention may be administered to the subject at any site, particularly a site that is "distal" to or "distant" from the primary tumor.

The route of administration of a pharmaceutical composition may be parenteral, intramuscular, subcutaneous, intradermal, intraperitoneal, intranasal, intravenous (including via an indwelling catheter), via an afferent lymph vessel, or by another route that is suitable in view of the tumor being treated and the subject's condition. Because of low-level inflammation or induration that may occur for the few days after administration, relatively non-invasive methods are preferred, particularly subcutaneous routes.

The dose given is an amount "effective" in bringing about a desired therapeutic response, be it the stimulation of an immune response, or the treatment of cancer as defined elsewhere in this disclosure. For the pharmaceutical compositions of this invention, effective doses typically fall within the range of about $10^5$ to $10^{11}$ cells, including allogeneic lymphocytes, and tumor cells and other cells from the subject being treated, if present. Preferably, between about $10^6$ to $10^{10}$ cells are used; more preferably between about $1\times10^7$ and $2\times10^9$ cells are used; more preferably between about $5\times10^7$ and $2\times10^9$ cells are used; even more preferably between about $1\times10^8$ and $1\times10^9$ cells are used. Multiple doses when used in combination to achieve a desired effect each fall within the definition of an effective amount.

The various components of the cellular vaccine are present in an "effective combination", which means that there are sufficient amounts of each of the components for the vaccine to be effective. Preferably, at least about $10^6$, more preferably at least about $10^7$ but no more than $10^{10}$ allogeneic lymphocytes are present. Preferably, at least about $10^5$, more preferably at least about $10^6$, and still more preferably about $10^7$ but generally less than $10^8$ and typically less than $5\times10^7$ tumor cells, tumor cell progeny, or the equivalents thereof are present. If autologous or third-party stimulator leukocytes are present, preferably there are between about $10^5$ and $10^8$. Ratios of allogeneic lymphocytes to stimulator leukocytes is generally between 1:1 and 100:1, usually between about 5:1 and about 25:1, and typically about 10:1. However, any number of component cells or other constituents may be used, as long as the vaccine is effective as a whole. This will also depend on the method used to prepare the vaccine, such as whether the allogeneic lymphocytes and autologous leukocytes are cocultured before administration.

The effectiveness of the composition is probably related to the proximity of the stimulated lymphocytes and the tumor antigens once administered to the subject. While it is most convenient to premix the components before administration, it is readily recognized that a similar effect is potentially achievable by separate administration to approximately the same vicinity in the subject. Accordingly, embodiments of this invention include not only compositions in which the components are premixed, but also combined preparations containing stimulated lymphocytes (such as alloactivated lymphocytes allogeneic to a human patient) and tumor antigen (such as primary tumor cells from the human patient or progeny thereof) for simultaneous, separate or sequential use in a method of treatment of a human by surgery or therapy, particularly for treating a tumor in the subject or eliciting an anti-tumor response.

The pharmaceutical compositions of this invention may be given following, preceding, in lieu of, or in combination with, other therapies relating to generating an immune response or treating cancer in the subject. For example, the subject may previously or concurrently be treated by chemotherapy, radiation therapy, and other forms of immunotherapy and adoptive transfer. Where such modalities are used, they are preferably employed in a way or at a time that does not interfere with the immunogenicity of the compositions of this invention. The subject may also have been administered another vaccine or other composition in order to stimulate an immune response. Such alternative compositions may include tumor antigen vaccines, nucleic acid vaccines encoding tumor antigens, anti-idiotype vaccines, and other types of cellular vaccines, including cytokine-expressing tumor cell lines.

Certain embodiments of this invention relate to combination therapies, comprising administration of a cellular vaccine combination described herein in conjunction with another strategy aimed at providing an anti-tumor immunological response. In one preferred combination therapy, the subject is given an intra-tumor implant of stimulated allogeneic lymphocytes, either before, during, or after treatment at a site distant from the tumor with a composition comprising stimulated allogeneic lymphocytes and autologous tumor cells. In another preferred combination therapy, the subject is treated at sites distant from the tumor with an alternative cellular vaccine composition, either before, during, or after treatment with a composition comprising stimulated allogeneic lymphocytes and autologous tumor cells. A preferred alternative composition for this purpose comprises autologous tumor cells mixed with allogeneic cells (particularly tumor cells) that have been genetically altered to express a cytokine at an elevated level. Where a plurality of different compositions or modes of administration are employed throughout the course of therapy, the order and timing of each element of treatment is chosen to optimize the immunostimulatory or anti-tumor effect.

Timing of administration of compositions of this invention is within the judgment of the managing physician, and depends on the clinical condition of the patient, the objectives of treatment, and concurrent therapies also being administered. Typically, at an appropriate time in patient management, a first dose is given, and the patient is monitored for either an immunological or clinical response, often both. Suitable means of immunological monitoring include a one-way MLR using patient's PBL as responders and primary tumor cells as stimulators. An immunological reaction may also be manifest by a delayed inflammatory response at the injection site. Suitable means of monitoring of the tumor are selected depending on the tumor type and characteristics, and may include CT scan, magnetic resonance imaging (MRI), radioscintigraphy with a suitable imaging agent, monitoring of circulating tumor marker antigens, and the subject's clinical response. Additional doses may be given, such as on a monthly or weekly basis, until the desired effect is achieved. Thereafter, and particularly when the immunological or clinical benefit appears to subside, additional booster or maintenance doses may be given as required.

When multiple doses of a cellular vaccine are given to the same patient, some attention should be paid to the possibility that the allogeneic lymphocytes in the vaccine may generate an anti-allotype response. The use of a mixture of allogeneic cells from a plurality of donors, and the use of different allogeneic cell populations in each dose, are both strategies that can help minimize the occurrence of an anti-allotype response.

During the course of therapy, the subject is evaluated on a regular basis for side effects at the injection site, or general side effects such as a febrile response. Side effects are managed with appropriate supportive clinical care.

The examples presented below are provided as a further guide to a practitioner of ordinary skill in the art, and are not meant to be limiting in any way.

EXAMPLES

Example 1

Cancer Treatment with Implants of Mixed Lymphocytes

This example describes a human study in which allogeneic lymphocytes stimulated in a mixed lymphocyte culture were implanted into the tumor bed of advanced brain cancer. As a result, the local environment comprised both the stimulated lymphocytes and any residual autologous tumor cells. This treatment was effective in limiting or reversing tumor progression and improving survival in some of the subjects treated. Coinciding observations support the present invention; particularly the apparent active involvement of the subjects own antitumor response.

A clinical trial was performed on patients with recurrent high grade astrocytomas to evaluate the feasibility, tolerability and toxicities associated with direct intratumoral implantation of allogeneic lymphocytes activated against patient alloantigens by mixed lymphocyte culture. Results indicate that direct intratumoral implantation of MLC-activated allogeneic lymphocytes in patients with recurrent high grade gliomas is feasible and safe and appears to provide a clinical benefit.

Nine patients with biopsy proven high grade astrocytomas (Daumas-Duport grade III or IV) were randomly selected for intratumoral implantation of MLC-activated allogeneic lymphocytes following recurrence or progression of their astrocytomas after standard therapies. The trial was approved by the Institutional Review Board of the Hospital of The Good Samaritan, Los Angeles, Calif. All patients were enrolled with informed consent. Patient ages ranged from 24 to 67 years (mean 50 years) and there were 4 males and 5 females. Eight patients had grade IV astrocytoma (glioblastoma multiforme, GBM) and one patient had grade III astrocytoma (anaplastic astrocytoma). All patients had failed prior debulking surgeries, radiation therapy, chemotherapy, and immunotherapy (autologous LAK cells plus IL-2), and presented with progressively growing tumor. Karnofsky performance scores ranged from 60 to 80 (mean 72.6) at the time of immunotherapy. Patient characteristics are listed in Table 1:

TABLE 1

| Patient | Age | Sex | Dx* | Site** | Therapies Prior to Study*** | KPS**** |
|---------|-----|-----|-----|--------|------------------------------|---------|
| BTP-001 | 67  | m   | AA  | LTL    | RT, CT, GK (4 mo)            | 80      |
| BTP-002 | 53  | f   | GBM | LFL    | RT, GK (0.5 mo)              | 70      |
| BTP-003 | 40  | m   | GBM | RTL    | GK, RT, CT, GK, ITx, GK (0.5 mo) | 70  |
| BTP-004 | 45  | f   | GBM | RTL    | DBS, RT, CT, RT, GK (2 mo)   | 60      |
| BTP-005 | 61  | m   | GBM | LOL    | DBS, RT, GK, GK (0.5 mo)     | 70      |
| BTP-006 | 24  | f   | GBM | ROL    | CT, GK (7 mo)                | 80      |
| BTP-007 | 56  | m   | GBM | LTL    | RT, DBS, CT, GK (1.5 mo)     | 70      |

TABLE 1-continued

| Patient | Age | Sex | Dx* | Site** | Therapies Prior to Study*** | KPS**** |
|---|---|---|---|---|---|---|
| BTP-008 | 48 | f | GBM | LOL | RT, CT, GK (0.5 mo) | 80 |
| BTP-009 | 51 | f | GBM | RPL | DBS, RT, CT, GK (0.5 mo) | 70 |

*GBM = Glioblastoma Multiforme (astrocytoma, Daumas-Duport Grade IV); AA = Anaplastic Astrocytoma (astrocytoma, Daumas-Duport Grade III).
**LFL = Left Frontal Lobe; RFL = Right Frontal Lobe; RPL = Right Parietal Lobe; LTL = Left Temporal Lobe; ROL = Right Occipital Lobe; LOL = Left Occipital Lobe.
***DBS = Debulking Surgery; RT = External Beam Radiation Therapy; CT = Chemotherapy; ITx = Prior Immunotherapy (LAK cells + IL-2); GK = Gamma Knife Therapy (months prior to alloimplant).
****KPS = Karnofsky Performance Score (at time of immunotherapy).

The preparative-scale mixed lymphocyte culture was conducted as follows. Three days prior to implantation, a genetically unrelated donor was identified and was leukapheresed to obtain the desired number of leukocytes. Leukapheresis for approximately 2.5 hours routinely provided up to $10 \times 10^9$ mononuclear cells. At the same time, a unit of blood was obtained from the patient, and the buffy coat was obtained by centrifugation. The mononuclear cells from the donor and the patient were then obtained by centrifugation over FICOLL™-Hypaque gradients (density =1.077). Patient mononuclear cells were inactivated by treatment with mitomycin-C (MC, Mutamycin) at 10 μg/ml for 1 h at 37° C., and washed to remove excess drug. Donor mononuclear cells were then mixed with the MC-treated patient mononuclear cells at 10:1 to 20:1 ratio in AIM V medium (total cell density $=2 \times 10^6$ cells/ml. The cells were dispersed into plastic culture bags (Baxter), and placed at 37° C. in a humidified, 5% $CO_2$/95% air incubator. After a three day incubation, viable cells were recovered by centrifugation, counted, suspended in 4–5 ml of sterile patient plasma, and transported to the operating room.

At the time of implantation, calcium gluconate was added to initiate a clot. The clot was then minced in a sterile metal dish. Tumor was resected where possible, forming a cavity circumscribed by the tumor bed. The minced clot containing stimulated, allogeneic lymphocytes were placed within the cavity, and within or next to whatever tumor remained.

Clinical toxicities associated with intratumoral implants of MLC-activated allogeneic lymphocytes are documented in Table 2. At each dosage level, some patients experienced grade 1 and grade 2 toxicities. However, these were transient effects, and it is unclear whether these were effects of the immunotherapy or surgical reaction. The degree of cerebral edema at each dosage level was controlled by administration of moderate doses of dexamethasome (between 8 and 24 mg/day), which was maintained for up to several months.

TABLE 2

| | | Dexamethasone Dosage (mg/day) at | | | |
|---|---|---|---|---|---|
| Patient I.D. | Cell Dosage | 1 week | 1 month | 3 months | 6 months |
| BTP-001 | $2 \times 10^9$ | 24 | 20 | 6 | 16 |
| BTP-002 | $2 \times 10^9$ | 16 | 24 | 96 | — |
| BTP-003 | $2 \times 10^9$ | | 15 | 48 | 96 |
| BTP-004 | $4 \times 10^9$ | 16 | 2 | 4 | 16 |
| BTP-005 | $4 \times 10^9$ | 16 | 24 | — | — |
| BTP-006 | $4 \times 10^9$ | 8 | 6 | 8 | 8 |
| BTP-007 | $6 \times 10^9$ | 16 | 14 | 24 | — |
| BTP-008 | $6 \times 10^9$ | 24 | 14 | 14 | 8 |
| BTP-009 | $6 \times 10^9$ | 9 | 16 | 24 | 10 |

Toxicities did not appear to increase at higher dosages of cytoimplant up to $6 \times 10^9$ cells. Due to the physical limitations in obtaining lymphocytes from the donor, the maximum dosage implanted did not exceed $6 \times 10^9$ cells.

Figure 1B:
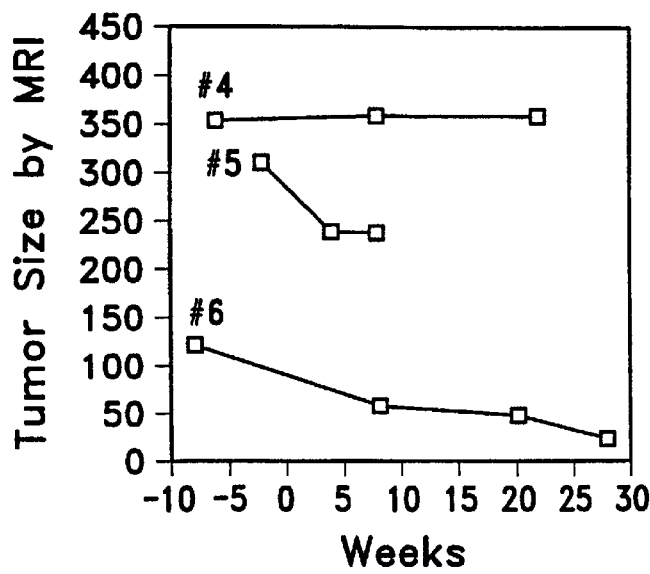
Figure 1C:
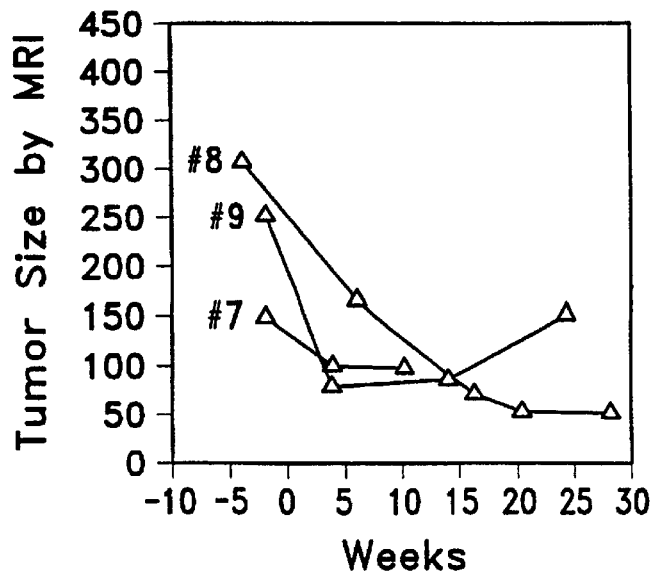

Clinical responses were evaluated by three criteria: a) serial MRI scans, using contrast enhancement with triaxial measurements of maximal enhancing diameter; b) Karnofsky performance scores; and c) survival. Tumor volumes from serial MRI scans for the 9 patients enrolled in the trial are shown in FIG. 1. MRI evidence of tumor response to the alloimplant (as assessed by gadolinium enhanced, T1 weighted MRI images) was seen in 3 of 9 patients. There was complete tumor regression in two patients and partial tumor regression (>50% shrinkage) in one patient over a 10 to 130 week observation period. In five patients, serial MRI scans showed stabilization of tumor size, with essentially no tumor growth over an 8 to 20 week observation period.

Only one patient showed progressive tumor growth after alloimplantation. The overall mean survival for the patients at each dosage level measured from the time of immunotherapy was 24 weeks at $2 \times 10^9$ cells (range 18–24 weeks), 64 weeks at $4 \times 10^9$ cells (range 10–135 weeks), and 72 weeks at $6 \times 10^9$ cells (20–140 weeks). Importantly, there were two long term survivors; one at the $4 \times 10^9$ cell dosage (BTP-006, >125 weeks), and one at the $6 \times 10^9$ cell dosage (BTP-008, >135 weeks).

Clinical toxicities associated with the intratumor cytoimplants are listed in Table 3. Toxicities were graded according to the following criteria: Grade 0= No headache, no fever, no seizures; Grade 1= Mild headache; Grade 2= Headache, Mild edema (MRI); Grade 3= Severe headache, moderate edema (MRI); Grade 4= Severe headache, severe edema (MRI), neurological changes. Irreversible Grade 3 or Grade 4 toxicity was dose-limiting.

TABLE 3

| Patient I.D. | Cell Dosage | Toxicities Observed | Survival* (weeks) | Response** |
|---|---|---|---|---|
| BTP-001 | $2 \times 10^9$ | Grade 1 | 77 | SD |
| BTP-002 | $2 \times 10^9$ | Grade 2 | 31 | PR |
| BTP-003 | $2 \times 10^9$ | Grade 1 | 113 | SD |
| BTP-004 | $4 \times 10^9$ | Grade 2 | 75 | SD |
| BTP-005 | $4 \times 10^9$ | Grade 1 | 75 | SD |
| BTP-006 | $4 \times 10^9$ | Grade 2 | 184+ | CR |
| BTP-007 | $6 \times 10^9$ | Grade 2 | 130 | SD |
| BTP-008 | $6 \times 10^9$ | Grade 2 | 160 + | CR |
| BTP-009 | $6 \times 10^9$ | Grade 2 | 48 | PD |

*Survival (in weeks) from time of initial diagnosis. + indicates currently live patients.
**Response to immunotherapy. CR = complete response; PR = partial response; SD = stable disease; PD = progressive disease.

Each of these patients were upgraded in their Karnofsky performance scores from 80- (preimplant) to 100. Two patients are currently alive and enjoying a good quality of life. Serial MRI scans of patient BTP-006 indicated continued tumor regression over a 24 month period. Serial MRI scans of patient BTP-008 also indicated a slow, persistent reduction in tumor size over a 24 month observation period.

Histology of the implant site was determined following an autopsy performed on a patient who died 60 days after implantation. Immunohistochemistry was performed on tissue sections fixed in 10% neutral buffered formalin. Five µm sections were prepared on siliconized glass slides and stained with primary antibodies against different cellular antigens using a TECHMATE™ automated immunostaining system (Biotech solutions, Inc., Santa Barbara, Calif.) composing the avidin-biotin complex method with DAB as the chromogen. Primary antibodies used included anti-CD68 (HAM 56, macrophages), L26 (CD20, B cells), UCHL-1 (T cells) and GFAP (glial cells). After immunostaining, the tissue sections were counterstained with hematoxylin, and examined microscopically for immunopositive cells. The identification of other inflammatory cell types and the extent of tissue necrosis were determined in parallel by histologic criteria using standard hematoxylin/eosin stained tissue sections.

Near the operative site where the alloimplant was placed, a cystic cavity was found, filled only with fibrin and organizing blood clot. Microscopically, no evidence of residual implanted lymphoid cells were present. However, sections taken from the periphery of the tumor, 1.5 cm away from the implant site showed massive infiltration of the tumor tissue by CD68+ macrophages and scattered lymphocytes, and evidence of extensive tumor necrosis. Interestingly, numerous CD68+ macrophages (microglia) were identified, apparently migrating from adjacent vessels in normal brain parenchyma toward areas of dying tumor tissue.

This study demonstrates that intratumoral implantation of MLC-activated allogeneic lymphocytes is feasible and well tolerated by the patients. Toxicities associated with the alloimplant included occasional headache, low grade fever and cerebral edema which was controlled by the administration of glucocorticoids. Long term surviving patients remained on steroids for many months after implantation but were eventually tapered to very low maintenance dosages. The procedure was associated with a significant number of responses as determined by tumor responses noted on serial MRI scans and, most importantly, prolonged patient survival.

Example 2

Genetic Alteration of Cells to Express Cytokines

In certain embodiments of this invention, one cell population or another is genetically altered to express a cytokine at an elevated level. This example provides two non-limiting illustrations of how cell populations may be genetically altered to express a cytokine. The illustrations alternatively make use of the pLXSN plasmid derived from a Maloney murine leukemia virus, or the LNCX retroviral expression vector. Genetically altered cells are produced that express the desired product in a stable fashion, even after cell division or irradiation.

IL-4 Secreting Cell Line

A human ovarian cancer cell line was genetically altered to secrete IL-4, using a retroviral vector comprising an IL-4 encoding construct. The cell line was stable, and capable of IL-4 biosynthesis even after an inactivating dose of radiation. The cell line expresses MHC Class I and Her-2/neu antigens, but no MHC Class II antigens, ICAM-1, CA-125, or IL-4 receptors.

Details of techniques useful for production of such cell lines are described elsewhere (Santin et al., 1995b & c). Briefly, the human ovarian cell line UCI-107 was established from a previously untreated patient with a primary Stage III serous papillary adenocarcinoma of the ovary. The UCI-101 and UCI-107 cell lines have been previously characterized by Gamboa-Vujicic et al. and were kindly provided by Dr. Alberto Manetta (University of California, Irvine Medical Center). Cells were maintained at 37° C., 5% $CO_2$ in complete media (CM) containing RPMI 1640 (Gibco Life Technologies), 10% fetal bovine serum (FBS, Gemini Bioproducts, Calabassas, Calif.), and 1 percent penicillin/streptomycin sulfate (Irvine Scientific, Santa Ana, Calif.).

Retroviral vectors were constructed as follows: The pLXSN plasmid was kindly provided by Dr. A. Dusty Miller (Fred Hutchinson Cancer Center, Seattle, Wash.). This plasmid, derived from a Maloney murine leukemia virus (MMLV) contains the neophosphotransferase gene whose constitutive expression is driven by the SV40 enhancer/promoter, the 5' retroviral LTR of the integrated vector drives the expression of an inserted gene. The human IL-4 cDNA was obtained from ATCC in the Okaiama and Berg pCD cloning vector, and was excised using BamHI restriction enzyme. The cDNA was then cloned into the BamHI restriction site in the multiple cloning region of pLSXN. Proper orientation of the cDNA was determined by diagnostic restriction endonuclease digests. Once constructed, retroviral plasmid DNA was then purified by CsCl gradient density centrifugation.

Purified retroviral plasmid DNA (LXSN/IL-4) was used to transduce the murine esotropic packaging cell line GP-E86 by the calcium phosphate method. Forty-eight-hour supernatant from these cells was then used to infect the murine amphotropic-packaging cell line, PA317. The PA-317-packaging cell line was obtained from the ATCC and maintained in CM. Transduced PA317 cells were selected by resistance to G418. Isolated clones were expanded, aliquoted, and frozen under liquid nitrogen in a master cell bank. The supernatant from a transduced PA317 clone, containing infectious, replication-incompetent retrovirus, was used to infect the human carcinoma cell lines. Briefly, human ovarian carcinoma cell lines were seeded in 100-mm tissue culture dishes at densities of $1 \times 10^6$ cells in 10 ml CM and incubated for 4 hr at 37° C., 5% $CO_2$ to allow adherence. After incubation, the medium was aspirated and replaced with 5 ml of 2% polybrene in phosphate-buffered saline (PBS), (Aldrich Chemical Co. Inc., Milwaukee, Wis). After 30 min at 37° C., 5% $CO_2$, 10 ml of retroviral supernatant was added, and retroviral-mediated gene transfer was accomplished by overnight incubation. Supernatants were then aspirated and replaced with CM. After an additional 48-hr incubation in CM at 37° C., 5% $CO_2$, selection of transduced clones was accomplished by culture in CM containing 0.075% G418 (geneticin, Gibco Life Technologies). Clones were isolated after 14 days using sterile 8×8 8-mm cloning cylinders (Belco Glass, Inc., Vineland, N.J.) and expanded for 3 weeks in CM containing G418. Parent cell lines were used as positive controls for G418 resistance. After clonal selection in G418, transduced cell lines were returned to CM for expansion and study.

Cells were established in CM at a density of $0.5 \times 10^6$ cells/10 ml in 100 mm tissue culture dishes. Cell counts were conducted every 12, 24, 48, 72 and 96 hours, and the number of viable cells was determined using trypan blue exclusion. Experiments were conducted to compare the growth of non-transduced (parental) and transduced tumor cell lines and to evaluate the level of cytokine production over time. Supernatants were collected and frozen at −20° C. (for subsequent ELISA evaluation of cytokine levels) and culture dishes trypsinized to determine cell count and viability.

Parental, IL-4 transductants, and vector control cells, were seeded in 100 mm tissue culture dishes (Corning) at a density of 1×10⁶ cells/ml in 10 ml CM. After 48 hour incubation at 37° C., 5 percent $CO_2$, supernatant was aspirated, rendered cell-free by centrifugation at 1,500 rpm for 10 minutes, then stored at −20° C. IL-4 concentration was then determined by ELISA, employing a commercially available kit (Research & Diagnostic Systems, Minneapolis, Minn.). Table 4 shows the level of secretion of Interleukin-4 from individual clones of genetically altered human serous papillary ovarian cancer cells

TABLE 4

| UCI-101 clones | | UCI-107 clones | |
| --- | --- | --- | --- |
| Designation | IL-4 pg/mL | Designation | IL-4 pg/mL |
| A | 140 | A | 32 |
| B | (not detectable) | B | 83 |
| C | 49 | C | 90 |
| D | 40 | D | 35 |
| E | 87 | E | 1300 |
| G | 93 | F | 30 |
| H | 38 | G | 80 |
| I | 93 | H | 513 |
| L | 42 | L | 170 |
| M | 32 | M | 297 |
| N | (not detectable) | N | 265 |
| O | (not detectable) | P | 330 |
| | | Q | 615 |
| | | X | 79 |
| | | Y | 68 |
| Average | 51.1 | Average | 265.8 |

As expected, each parental line and cells transduced with vector alone did not produce detectable levels of IL-4. The best IL-4 producing clone, termed UCI 107E IL-4 GS, was expanded and employed to form a master cell bank for further testing and extensive characterization.

The parental cell line UCI 107 has the characteristic morphology of ovarian epithelial cells grown in vitro. The morphology of UCI 107 cells transduced with the LXSN vector alone or LXSN containing the IL-4 gene was indistinguishable from that of parental 107 cells. The doubling time of parental, vector control, and UCI 107E IL-4 GS cells was determined to be 15.3, 15.7, and 18.6 hr, respectively.

No changes in the growth rate of these cells have been observed in vitro over 35 passages and 6 months of culture. Levels of IL-4 production were consistently in the range of 900 to 1300 pg/ml/10⁵ cells/48 hr during the 6 months of passage. Extensive tests performed on the UCI 107E IL-4 GS master cell bank (MCB) revealed that this line is free of the presence of mycoplasma, bacteria, and infectious viruses.

Southern analysis was conducted using the $Neo^R$ gene to probe the UCI 107E IL-4 and the parental UCI 107 line. Briefly, concentrated suspensions of tissue culture cells were lysed in TNE buffer (10 mM Tris, 100 mM NaCl, 1 mM EDTA, pH 7.5) containing 0.5% SDS, treated with 50 µg/ml proteinase K overnight at 37° C., then extracted with phenol and chloroform. The DNA solution was precipitated in 100% ethanol, spooled out and resuspended in 10 mM Tris, 0.1 mM EDTA (pH 8). Ten jig of high molecular weight DNA was digested with SstI (GIBCO/BRL, Grand Island, N.Y.), separated by electrophoresis on a 0.8% agarose gel and transferred to Gene Screen Plus (Dupont NEN, Boston, Mass.). Transfer, hybridization, and washing were performed according to manufacturer's specifications. Random primer IL-4 probe was prepared by the method of Tabor and Struhl (1988) In Current Protocols in Molecular Biology Vol.1. pp.2.2.1–2.2.3. The results confirmed that after 20 passages, UCI 107E IL-4 still contained the vector DNA.

Stability of IL-4 secretion after irradiation was tested as follows: Cells were irradiated in a 15 ml conical tube in CM at room temperature with gamma rays ($^{137}Cs$) at a dose rate of 200 rads/minute. Immediately after irradiation, cells were seeded in a Petri dish culture plate at a density of 1×10⁶ cells in 10 ml of CM. Test doses of 1,000 to 10,000 rads were applied. Irradiated cells were cultured at 37° C. in a 5% $CO_2$ atmosphere and the medium was completely changed every four days in all the dishes. Every 48 hours, culture supernatants were collected from the dish for cytokine production and the number of viable cells was assessed by light microscopy by trypan blue exclusion.

Figure 2A:
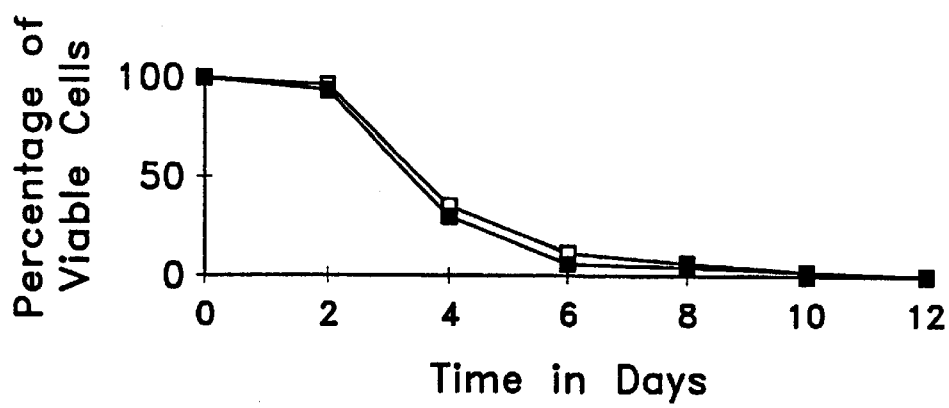
FIG. 2 is a three-panel graph showing the effects of irradiation on an established IL-4 secreting tumor cell line. Panel A shows the growth pattern of cells given 5,000 (□) or 10,000 (■) rads. Panels B and C show IL-4 detected by ELISA in the culture medium expressed as total concentration (Panel B) or per cell (Panel C) various times after irradiation.
Figure 2B:
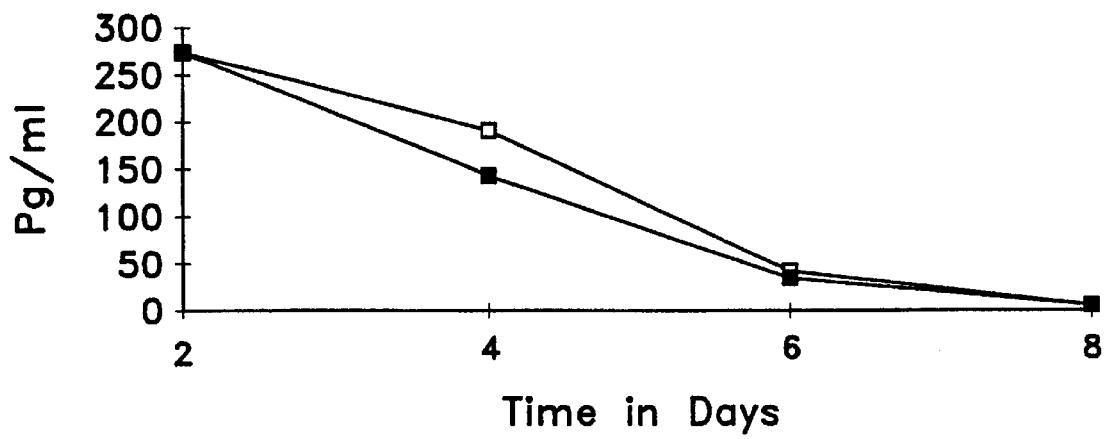
Figure 2C:
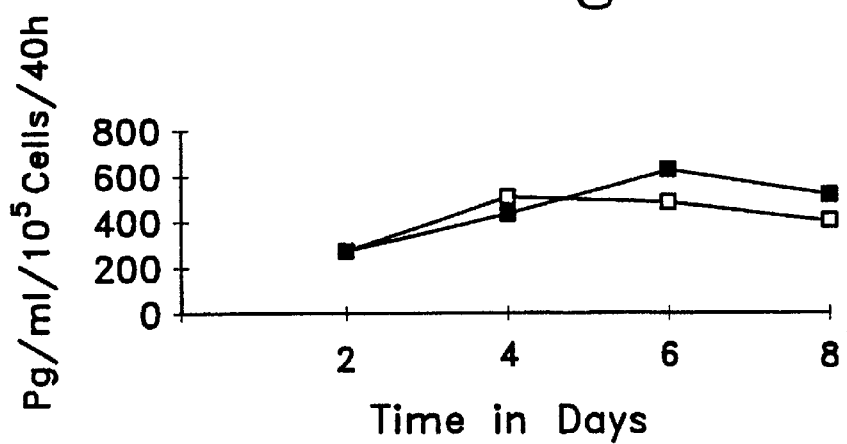

Results of this experiment are shown in FIG. 2. Cells irradiated with between 2,500 and 10,000 rad remained viable for about 8 days but all the cells were dead by 3 weeks. Cells irradiated with 1,000 rad recuperated and continued to proliferate. Levels of cytokine production were detectable for 8 days at all doses and closely paralleled the number of viable cells. Panel B shows IL-4 production after irradiation at 5,000 rad (□) or 10,000 rad (■) in three separate experiments. Panel C shows IL-4 production standardized in pg/ml/10⁵ cells/48 hr by UCI 107E IL-4 GS cells after irradiation at 5,000 or 10,000 rad in two separate experiments. No statistically significant differences in survival were seen among cells irradiated with 2,500, 5,000, and 10,000 rad on days 2 (p=0.72), 4 (p=0.14), 6 (p=0.10), and 8 (p=0.3).

Collectively, these results indicate that UCI 107E IL-4 GS cells constitute a stable IL-4 secreting cell line. The cells can be irradiated to stop replication effectively, yet maintain IL-4 production for up to a week.

TNF-α Secreting Cell Line

A human TNF-α encoding sequence was used to genetically alter a rat glioblastoma line, and shown to confer protection against several different glioma lines. Graf et al. (1994) Soc. Neuroscience (abstract).

Briefly, the TNF-α encoding sequence was inserted into a TNF insensitive Fischer rat T9 glioblastoma cell line by retroviral-mediated gene transduction, using an LNCX retroviral expression vector. A clone designated T9/LNCT2 was isolated that secretes biologically active TNF at a level of 2,000 pg/106 cells/48 h. The growth rates of the transduced cells, T9 parental cells, and cells transduced with the vector alone (designated T9/LNCX) were identical. The T9/LNCT2 line has been maintained for a full year without loss of TNF secretion capacity.

When parental or vector control T9 cells were injected subcutaneously in the flank of Fischer rats, tumors became established and grew to kill the animals. In contrast, T9/LNCT2 cells injected subcutaneously grew initially, but regressed in 40–50% of the animals in 3–4 weeks. TNF was secreted by the subcutaneous T9/LNCT2 cells during this period. Survivors were totally resistant to intracranial rechallenge with parental T9, even after 1 year. In addition, these animals were also resistant to challenge with the syngeneic glioma cell line, 9L.

Example 3

Resistance to Rechallenge After Treatment with a Cytoimplant

A rat model for cancer treatment was developed by injecting the metastatic breast carcinoma cell line MADB $10^6$ L.$^{-1}$ into the median lobe of the liver of the Fisher 344 inbred rat strain. Tumors were measured regularly, and established for 14 days before treatment.

Mixed lymphocyte cultures were prepared using inactivated Fisher 344 stimulator lymphocytes and Wistar-Furth (W/F) allogeneic responder lymphocytes at a 1:1 ratio. Three days after initiation of the culture, 80–$10^6$ cells were injected directly into established, progressively growing tumors. Groups of 5 rats were treated as follows: Group 1 received no injection; Group 2 were injected with unsensitized allogeneic W/F lymphocytes directly into the tumor; Group 3 were injected similarly with cells obtained from the mixed lymphocyte reaction.

The effect of MLC treatment on survival is shown in Table 5:

TABLE 5

|  | Group 1 (Untreated) | Group 2 (Unsensitized lymphocytes) | Group 3 (MLC) |
|---|---|---|---|
| Median survival (days) | 38 | 51 | 68* |
| Range (days) | 17–62 | 32–63 | 55–300+ |
| Long-term survivors | 0% | 0% | 20% |

* Log Rank Sum test Groups 1 & 2: p < 0.02

The MLC-treated group was the only group with long-term survivors. The survivors were resistant to rechallenge with parental tumor cells. It was conclude that direct intratumoral implantation of allogeneic lymphocytes stimulated via a mixed lymphocyte culture confers a significant survival advantage. The effect may be mediated through immune activation of host anti-tumor immunity in response to activated lymphocytes and cytokine production in the local tumor microenvironment.

Example 4

Cellular Vaccination at Sites Distant from the Tumor

This example establishes the use of a cellular vaccine comprising stimulated allogeneic lymphocytes mixed with syngeneic tumor cells in a mouse model, and identifies an amount effective in generating an immunological response and conferring tumor resistance.

General materials and procedures are as follows. About 1 to $2 \times 10^8$ spleen cells are typically recovered from a single mouse spleen. Responder and stimulator spleen cells are mixed and cultured in 1 mL RPMI medium supplemented with 10% fetal calf serum and 1 mM BME in a $CO_2$ incubator at 37° C. for 3 days. Culture supernatants are analyzed by ELISA for IL-2, TNF, IFN-γ and IL-4. Cell-surface CD markers in the cultured cells are determined by flow cytometry analysis. Cells are also monitored by morphological criteria to determine the number of small lymphocytes, blast cells, and apoptotic bodies. The requisite number of cells from the mixed lymphocyte culture are combined with tumor cells in phosphate-buffered saline at a final injection volume of about 100 μL. The composition is administered by injection subcutaneously into the right flank. The injection site is examined for signs of inflammation, and spleen cells are collected periodically for determination of immunological criteria. Biopsy and autopsy samples are examined both by standard morphological criteria and by immunohistology.

J588L is a plasmacytoma cell line derived from a spontaneous tumor in a Balb/c mouse. Subcutaneous injections of $10^6$ viable J588L cells form palpable tumors greater than 5 mm in diameter in 100% of histocompatible mice treated within about 12 days, accompanied by cellular necrosis. In experiments of this type, mice are sacrificed after tumors reach ~10 mm in diameter.

In one experiment, Balb/c mice were injected subcutaneously with $10^6$ J588L plasmacytoma cells admixed with $10^6$ cytoimplant cells. The cells for the cytoimplant were generated by coculturing C57BL/6 splenocytes with Balb/c splenocytes at a 10:1 ratio for 3 days. Tumor growth at the injection site was measured in mice treated with the cell mixture, and compared with that of mice injected with $10^6$ J588L cells mixed with $10^6$ C57BL/6 splenocytes alone, as a control. All 15 of the mice in the control group had tumors of at least 1 cm in diameter within 14 days. However, 11 out of 15 mice in the former group had no tumor growth; the other 4 mice had tumors that grew slower than in the controls. Surviving mice in this group were subsequently challenged with an additional bolus of J588L cells in the opposite flank to determine whether there was an ongoing systemic immunological response against the tumor. Seven out of the 10 mice were resistant to rechallenge, showing no tumor growth, or limited growth followed by regression.

Further characterization of the interrelationship between cells of the cytoimplant and the response obtained is performed by testing the combinations shown in Table 6.

TABLE 6

| Mixed Lymphocyte Culture (Cytoimplant Cells) | | | Predicted |
|---|---|---|---|
| Stimulator Cells | Responder Cells | Ratio | Initial Effects |
| Balb/c ($H2^d$, $IA^d$) (syngeneic) | C57BL/6 $H2^b$ (allogeneic) | 1:1 1:10 1:20 | graft vs. host graft vs. tumor host vs. graft cytokine secretion |
| Balb/c ($H2^d$, $IA^d$) (syngeneic) | C3H/He $H2^k$ (allogeneic) | 1:1 1:10 1:20 | graft vs. host graft vs. tumor host vs. graft cytokine secretion |
| C57BL/6 ($H2^b$) (allogeneic) | C3H/He $H2^k$ (allogeneic) | 10:1 1:1 1:10 | cytokine secretion |
| Balb/c ($H2^d$, $IA^d$) (syngeneic) | DBA/2 $H2^d$ minor histocompatibility antigen incompatible | 1:1 1:10 1:20 | graft vs. host graft vs. tumor host vs. graft cytokine secretion |
| none | C57BL/6 $H2^b$ (allogeneic) |  | allostimulus |

$10^6$ cultured cells are mixed with $10^6$ J588L cells and injected into Balb/c mice, and their response is monitored as before. Surviving mice are tested for ongoing immunity and tumor resistance by a subsequent challenge with $10^6$ J588L cells alone.

A second set of experiments is directed towards determining the benefit of including modulators in the vaccine composition. T helper cells may be functionally divided into two subsets. $T_H1$ cells may be elaborated in the presence of IL-2, IFN, or IL-12, and are believed to favor cellular cytotoxicity in vivo. $T_H2$ cells may be elaborated in the presence of IL-4, IL-5, or IL-10, and are believed to favor B cell secretion. $T_H1$ cells may predominate during typical in vitro mixed lymphocyte cultures because of the presence of IL-2. $T_H2$ cells may play a role in strong antitumor immunity through the production of IgE and involvement of eosinophil-mediated tumor cytolysis.

Experiments are conducted in which the mixed lymphocyte culture used to provide the stimulated allogeneic lymphocytes of the vaccine composition is supplemented with relevant modulators, particularly IL-2, IL-4, or prednisone. The level of modulators is first tested in the ranges used by Piccinni et al. (1995) *J. Immunol.* 155:128 ff. and Spits et al. (1988) *J. Immunol.* 141:29–36. C57BL/6 splenocytes with Balb/c splenocytes are cocultured at a 10:1 ratio in medium supplemented with each test mediator beginning at day 0 of the culture. IL-2 is expected to enhance the proportion of $T_H1$ cells, while IL-4 or prednisone are expected to enhance the proportion of $T_H2$ cells, compared with unsupplemented cultures. The characteristics of each culture are determined by measuring cytokine levels in the supernatant by immunoassay or bioassay: for example, IL-2 (secreted by $T_H1$), IL-4, IL-5 (secreted by $T_H2$), IFN-γ, or TNF-α. The characteristics of each culture are also determined by cell surface markers by flow cytometry: for example, CD45RB (higher on $T_H1$ than $T^H2$); CD-69, and IL-2 receptor (elevated on activated cells).

Protection experiments are conducted as follows: $10^6$ cultured cells are mixed with $10^6$ J588L cells and injected into Balb/c mice, and their response is monitored as before. Surviving mice are tested for ongoing immunity and tumor resistance by a subsequent challenge with $10^6$ J588L cells alone. Specificity of the immunological response is tested by challenging immune mice with unrelated tumor lines. The effect of vaccines made from cultures enriched for $T_H1$ cells is compared with vaccines made from cultures enriched for $T_H2$ cells. Additional experiments are conducted in which animals are treated with a composition comprising cells combined from both types of cultures, along with the J588L plasmacytoma cells.

Example 5

Measurement of the Degree of Alloactivation

In order to ensure the production of high quality effective MLC cells, a method of measuring the potency of the alloactivated cells can be employed. Only cell cultures with activity over and above unstimulated control cells should be used clinically. It is beneficial to compare the activity to the unstimulated control, since baseline activity of mononuclear cells from different individuals varies widely.

Several methods are available for measuring lymphocyte activation. Compared with unstimulated mononuclear cells, alloactivated cells reduce more Formazan dye and have more esterase activity. Turnover of XTT (a Formazan dye) can be easily demonstrated in a 96-well plate by calorimetric spectrophotometry at 470 nm (reference 650 nm). Activated cells typically show higher absorbance than controls. Lymphocyte activation can also be demonstrated by flow cytometric determination of esterase activity using the esterase substrate, fluorescein diacetate (FDA). T cells with high esterase are not determined using FDA and a Phycoerythrin-labeled CD3 antibody. Esterase activity can be accurately measured in a plate assay by using higher concentrations of FDA and determination of esterase activity by spectrophotometry at 494 nm (reference 650 nm) in a 96-well plate format. Background esterase activity inherent to serum-containing media is inhibited by addition of a competitive esterase inhibitor (~10 mM), arginine methyl ester. For the most part, these measures show good correlation with each other and with blastogenesis.

I: MTT Formazan Reduction Assay

This assay is used to enumerate live cells by ability for culture sample to reduce MTT to blue-green Formazan dye, and is also helpful for the distinguishing activated from inactive cells. It can be used for practically any cell in practically any media. The useful cell range is between $10^5$ and $5 \times 10^6$ per mL.

Reagents:
  96 well plates, flat bottom (not ELISA plates)
  5 mg/mL MTT (Sigma) in PBS (frozen)
  20% SDS in 45% DMF, 0.2 N HCl (pre-warmed to 37° C.)

Procedure:
  Place 100 μL of culture media with cells in 96 well plate in duplicate or triplicate. Use 100 μL of media alone for controls. Leave first column blank.
  Add 10 μL of MTT to each well. Tap plate to mix. Cover plate and incubate 37° C. for 4 hours.
  Add 50 μL of SDS solution, avoiding bubbles. Tap to mix. If bubbles are present, blow on surface. Count plate at 570 nm (reference 650 nm).

II: XTT Formazan Reduction Assay

This assay is used to enumerate live cells by ability for culture to sample to reduce XTT to red-orange Formazan dye, and is also helpful for the distinguishing activated from inactive cells. It can be used for practically any cell in practically any media. The useful cell range is between $10^5$ and $5 \times 10^6$ per mL.

Reagents:
  96 well plates, flat bottom (not ELISA plates)
  1 mg/mL MTT (2,3-bis (2-methoxy-4-nitro-5-sulfo-phenyl-2H-tetrasolium-5-carboxanilinide salt, Sigma) in PBS (fresh)
  1.53 mg/mL PMS (phenylmethanesulfonyl fluoride, Sigma) in PBS (frozen, protected from light)

Procedure:
  Place 100 μL of culture media with cells in 96 well plate in duplicate or triplicate. Use 100 μL of media alone for controls. Leave first column blank.
  Pre-mix PMS with XTT immediately before use (5 μL per mL XTT). Add 50 μL of XTT to each well. Tap plate to mix.
  Cover plate and incubate 37° C. for 4 hours. Count plate at 470 nm (reference 650 nm).

III: Flow Cytometry for CD3/CD69 or CD3/FDA

This is a measurement of T lymphocyte activation after mixed lymphocyte alloactivation. Activities such as CD69 expression or esterase activity correlate with cytokine secretion and can be used as surrogate measures of lymphocyte activity. Unstimulated lymphocytes do not express surface CD69 and have only low levels of non-specific esterases. Once activated by allo-antigens or non-specific mitogens, the expression of CD69 appears within 48 hours (peak at 24). Esterase activity increases shortly after stimulation, and continues for several days. Not all allostimulated lymphocyte reactions proceed with the same kinetics, and it is preferable to measure activation on day 1, 2 and 3 of the culture.

Sample:
  Test samples of donor and patient cells are mixed in small cultures at $0.5 \times 10^6$ cells/mL in 2% FCS-RPMI. These cultures are maintained at 37° C. in 5% $CO_2$ incubator until testing.

Reagents:
  Monoclonal antibodies:
  CD3-PE (Coulter)
  CD69-FITC (Becton-Dickinson). Keep refrigerated when not in use and protect from light.

Fluorescein Diacetate (Sigma): Stock solution is prepared at 10 mg/mL DMSO, protected from light, and stored in frozen lot tested aliquots. Make working solution weekly by diluting stock 1:100 in DMSO, keep working solution refrigerated and protected from light.

D-PBS, 0.5% paraformaldehyde-0.05% TRITON™ X-100 in PBS

Procedure:

Internal control unstimulated and activated mononuclear cells samples are produced on an as-needed basis. Large lot-tested batches will be frozen in 250 µl aliquots in 10% DMSO freezing media.

Mononuclear cells from a normal donors can be used to produce activated control specimens. These cells are placed in 2% FCS-RPMI at $0.5 \times 10^6$ cells/mL up to 100 mL. Cells are cultured for 2 days at 37° C. in the presence or absence of 2 µg/mL PHA lectin, or admixed at a ratio of 10:1 with a second donor population. The cells are collected by centrifugation at 350×g for 5 minutes. The media is removed and replaced by ⅒th the volume of DMSO Freezing media, and frozen. When needed, control unstimulated and stimulated cells can be thawed quickly and resuspended at the original volume by adding 9 volumes of PBS.

Control cells are analyzed according to the protocol below along with samples from the test culture. The duplicate use of control specimens is an addition quality assurance measure. The percentage of CD69 or esterase positive lymphocytes should be within a 5% variance.

Dilute 5 µL of CD3-PE antibody (per sample) in 0.5 mL PBS (per sample). Add either 10 µL CD69 (per sample) or 1 µL of working solution of FDA (per sample).

To 12×75 mm labeled polystyrene tubes, deliver 0.5 mL of diluted antibody. Add 100 µL of well mixed sample to each tube, including reference controls, unstimulated donor cells and the allo-activated cells. Gently vortex and incubate 30 minutes at room temperature. Add 0.5 mL of 0.5% paraformaldehyde-0.05% TRITON™ X-100 PBS and mix.

Counting is performed on an appropriately equipped flow cytometer, such as the EPICS XL Coulter Flow Cytometer. Histogram 1 (forward scatter vs. CD3) of either protocol should have a generous gate around the CD3+ mononuclear cells. Region A should approximate % T-Lymphocytes and should be passed to Histogram 2. In Histogram 2, the use of side scatter versus CD3 permits discrimination of lymphocytes (low side scatter level) from unlysed RBSs, RBC ghosts, platelet aggregates, residual granulocytes and/or other debris. A gate is drawn around the lymphocytes (see Histogram 2 for example). This second gate is passed to Histogram 3, where the CD3+ CD69+ cells or CD3+ FDA+ cells are displayed. Run the control values first to set gates (unstimulated controls). Place the quad stat cursor of Histogram 3 so that the CD69 or FDA high values (Quad 2) are 2%. Leave this gate set when analyzing stimulated samples.

Count at least 5,000 gated cells for each sample to obtain a 97% confidence interval.

IV: FDA Plate Assay

This assay is used to enumerate live cells by ability for culture sample to turnover the esterase substrate, fluorescein diacetate, and is also helpful for the distinguishing activated from inactivated cells. This assay can be used for practically any media. The useful cell range is between $10^5$ and $5 \times 10^6$ per mL.

Reagents:
- 96 well plates, flat bottom (not ELISA plates)
- 10 mg/mL FDA (Sigma) in DMSO (stock, protect from light)
- 10 mg/mL Arginine methyl ester (Sigma) in DMSO Procedure:

Place 100 µL of culture media with cells in 96 well plate in duplicate or triplicate. Use 100 µL of media alone for controls.

Make a fresh working solution of FDA by adding 10 µL per mL of PBS of stock FDA plus 50 µL AME stock per mL. Add 20 µL of FDA working solution to each well. Tap plate to mix.

Cover plate and incubate 37° C. for 1 hour. Count plate at 494 nm (reference 650 nm).

V: Acid Production Assay

This assay is used to quantitate relative organic acid production in cultures. This correlates with the state of activation of cells. This assay requires the use of medium containing no more than 2% serum. Practical cell range is $1-5 \times 10^6$ cells/ml incubated from 24–48 hours.

Reagents:
- 96 well plates, flat bottom (not ELISA plates)
- Acid Analysis Reagent. This is made in bulk and stored at 4° C. Add 0.1 mg/mL Bromophenol Blue in distilled water. Add sufficient concentrated HCl until the appropriate titration point is met. Titration is performed until yellow-green color is obtained after adding 75 µL of reagent to 100 µL RPMI 2% FCS in a well of a 96 well plate.

Procedure.

Place 100 µL of culture media with cells in 96 well plate in duplicate or triplicate. Use 100 µL of media alone for controls.

Add 75 µL of Reagent to each well. Tap plate to mix. Count plate at 470 nm (reference 650 nm).

VI: Blastogenesis Quantitation

This assay is used to quantitate the absolute number of lymphoblasts produced in cultures after 7 days. This assay can be used for peripheral blood mononuclear cells in practically any media. The useful cell range is between $1 \times 10^5$ and $5 \times 10^6$ per mL.

Reagents.
- Wright's Stain or Diff-Quick Stain

Procedure:

Place 1–2 drops of a 7 day culture in a Cytospin chamber and perform Cytospin. Stain dried glass slide with either Wright's Stain or Diff-Quick Stain. Count number of lymphoblasts and other cells under oil immersion 100× lens of microscope. Count over 300 total cells.

Example 6

Further Animal Model Experiments

Efficacy of Alloactivated Cells Prepared Using Third-party Stimulators

Cell compositions were prepared, composed of either unstimulated allogeneic cells alone, allo-activated syngeneic cells, syn-activated allogeneic cells or alloactivated allogeneic cells (two separate allogeneic cells), or all-activated allogeneic cells (two separate allogeneic donors). Splenocytes form the mice were used to produce the alloactivated cells by culturing at a ratio of 10:1 responder:stimulator cells. Splenocyte combinations were cultured in RPMI plus 10% fetal calf serum (FCS) supplemented with penicillin-streptomycin at $3 \times 10^6$/ml at 37° C. for 3 days.

$1 \times 10^6$ live J588L lymphoma cells were admixed with $10 \times 10^6$ cultured mouse splenocytes, and then injected into the subcutaneous tissue over the right flank of Balb/c mice. Treated mice were watched for tumor growth for 3 weeks.

Mice without tumor were rechallenged 1 month later with $1\times10^6$ live lymphoma cells alone by left flank subcutaneous injections, and watched for tumor growth.

Figure 3:
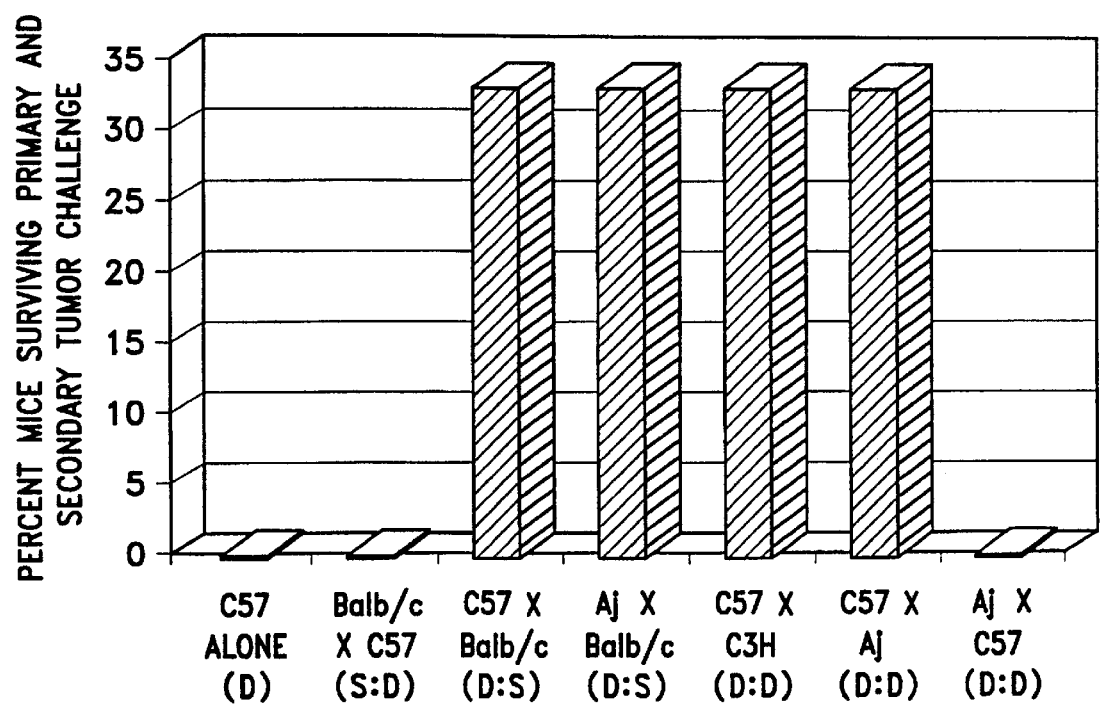
FIG. 3 is a bar graph showing the effect of different alloactivated lymphocyte preparations on providing resistance to a secondary challenge with J588L lymphoma cells in Balb/c mice. Allogeneic cells stimulated either with syngeneic splenocytes or certain third-party splenocytes are both effective.

FIG. 3 shows the results of these experiments. The presence of activated allogeneic cells correlates with a subsequent in vivo antitumor host response. Cell populations prepared using two donors allogeneic to the treated animal could be used in place of syngeneic or autologous cells in order to induce an antitumor response. However, not all combinations of activated allogeneic Donor:Donor cell populations were equally effective.

Effect of Ratio of Responder:Stimulator Cells on Efficacy

Cell populations were prepared composed of allogeneic cells activated by a variable number of syngeneic stimulator cells, using C57 splenocytes as the responder and Balb/c splenocytes as the stimulator. The cells were admixed with live lymphoma cells (J588L cells) and injected into the flanks of Balb/c mice. Treated mice were watched for tumor growth for 3 weeks.

Figure 4:
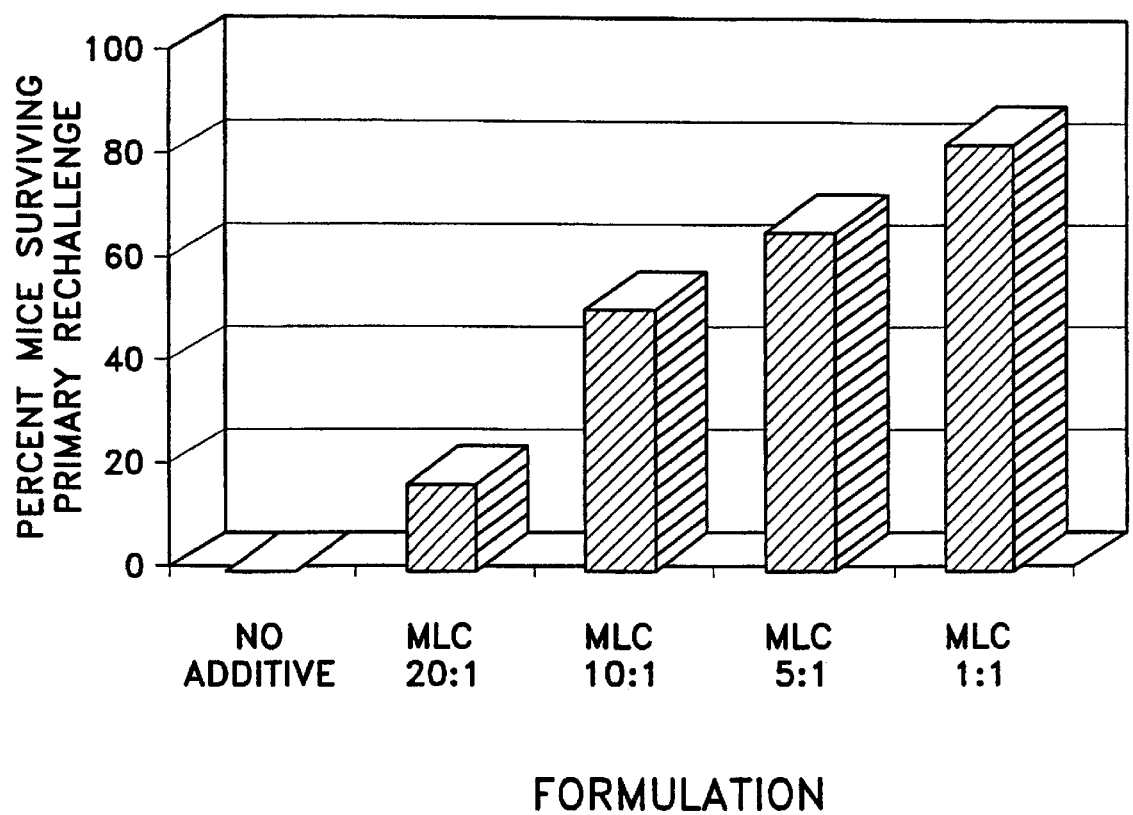
FIG. 4 is a bar graph showing the effect of different cell culture ratios on survival time in the mouse lymphoma model.
Figure 5A:
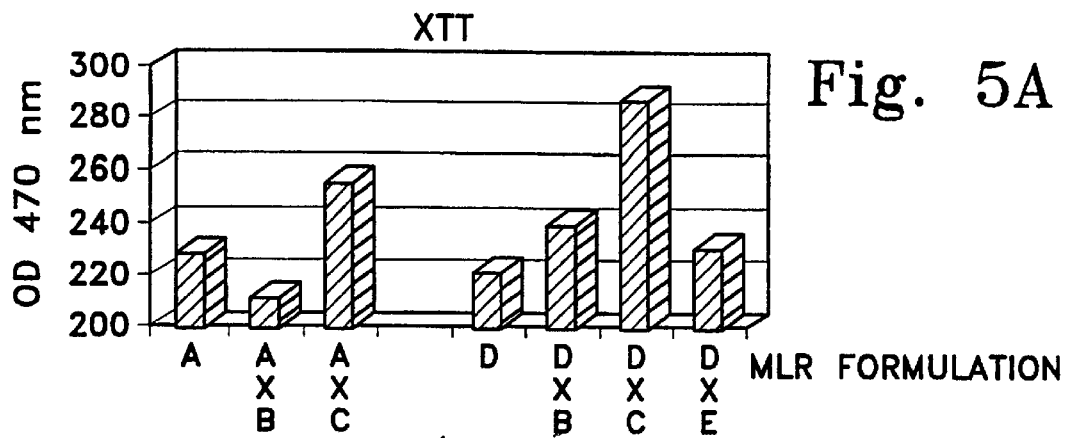
FIG. 5 is a bar graph showing the degree of functional activity in different human alloactivated cell preparations, as determined in four different assays.
Figure 5B:
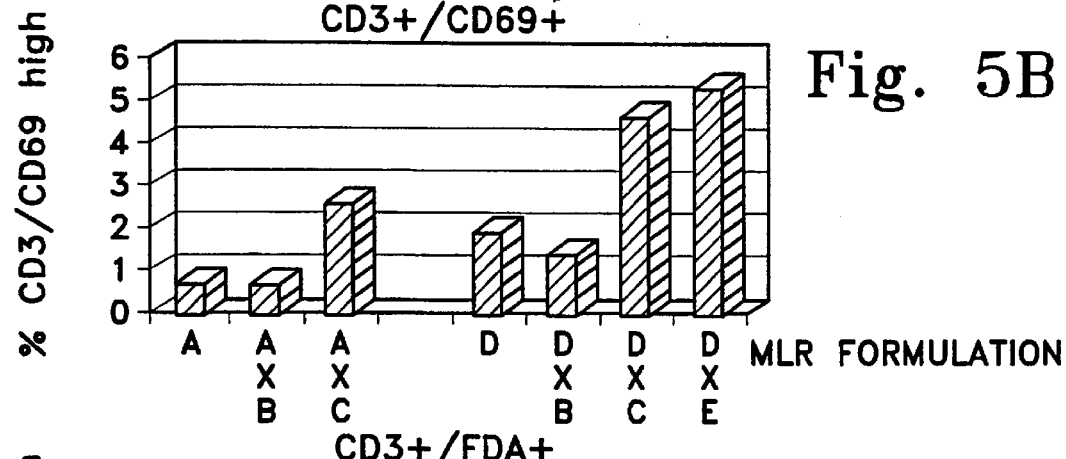
Figure 5C:
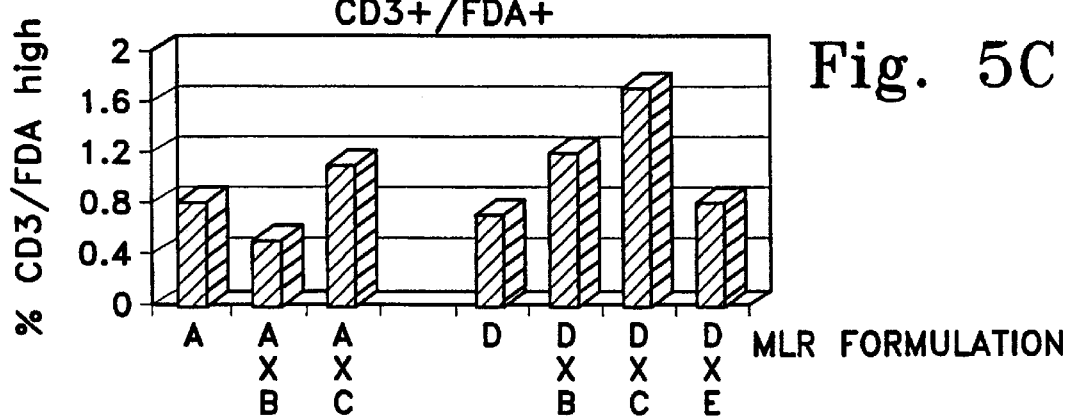
Figure 5D:
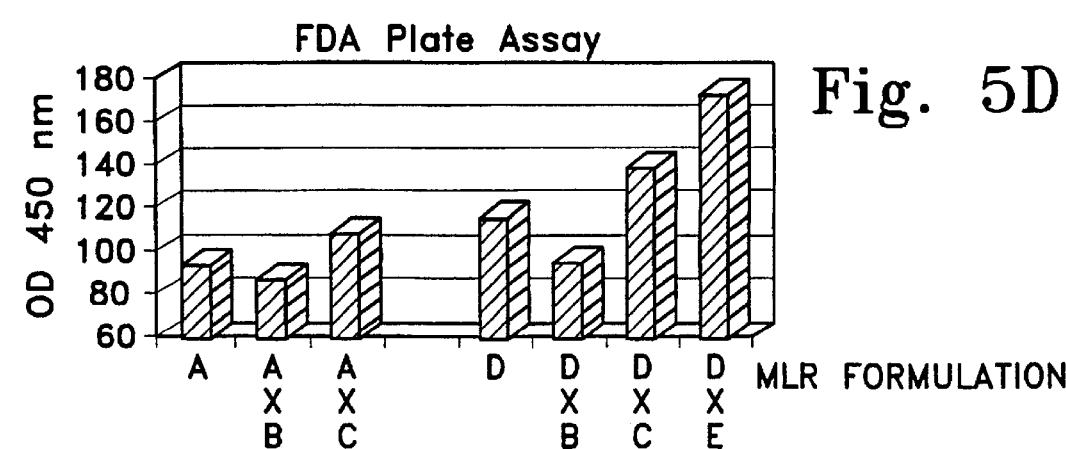

FIG. 4 shows the percentage of mice without tumors after primary tumor challenge (6 mice per group). A lower cell ratio may on some occasions be better at inducing an antitumor response in mice.

Impact of Using Splenocytes from Tumor-Bearing Mice on the Antitumor Effect

Splenocytes were taken from naive C57 or Balb/c mice or from a mouse bearing a 1 cm lymphoma in the right flank. The cells were cultured for 3 days either alone or after admixture with Balb/c cells at a 10:1 ratio at a concentration of $0.5\times10^6$ cells/mL in RPMI- 10% FCS. Lymphocyte activation was judged by analyzing the percentage of CD3+/Esterase high population by Flow Cytometry. The percent FDA positive cells was ~3.5% using stimulators from healthy Balb/c donors, but only ~2.5% using stimulators from tumor-bearing donors.

The cell populations alloactivated with stimulators either from naive Balb/c mice or from mice bearing J588L tumors were admixed with live lymphoma cells (J588L cells) and injected into the flanks of naive Balb/c mice. The mice were monitored for tumor growth for 3 weeks. Mice without tumors were next rechallenged with $1\times10^6$ live lymphoma cells alone in the left flank, and watched for tumor growth. Percent mice without tumors after secondary tumor challenge was between 30 and 40% in both groups.

Resistance of Mice Immunized with Alloactivated Lymphocytes and Irradiated Tumor Cells to Subsequent Tumor Challenge This experiment tested the immunogenic effect of a cell vaccine containing alloactivated lymphocytes mixed with inactivated tumor cells.

C57/BL6 mice (3 per group) were injected subcutaneously with $10^6$ irradiated B16 melanoma cells alone, mixed with $10^7$ Balb/c×C57 alloactivated lymphocytes, or mixed with $10^6$ IL-4 secreting J588L lymphoma cells (allogeneic to C57). The alloactivated cells were prepared by culturing Balb/c splenocytes with C57 splenocytes at a ration of 10:1 at $3\times10^6$/mL in RPMI 10% FCS for 3 days.

Cells were washed in PBS, and injected subcutaneously in the flanks of naive C57 mice. After 3 weeks, the mice were rechallenged with $5\times10^5$ B 16 live melanoma cells subcutaneously in the opposite flank. Mice were observed for tumor formation and sacrificed after tumors reached 1 cm in diameter.

The mice treated with the alloactivated cells survived significantly longer than the other groups. The two longest surviving mice finally developed cone-shaped tumors, both of which ulcerated. No other mice developed ulcers. Two days after the ulcers appeared, both mice expired. Necropsy of these mice revealed the presence of extremely necrotic tumor cells, with evidence of recent tumor cell lysis in the form of massive DNA deposition. This necrosis was accompanied by an inflammatory infiltrate, consisting mostly of lymphocytes. No other form of infection was observed anywhere in the body. No lung metastases were seen. This is in contrast to the large number of lung metastases in control mice harboring B16 melanoma tumors in the flank. Bilateral kidneys in both mice showed extensive glomerulonephritis, suggesting death from tumor lysis syndrome. No other mice demonstrated these changes.

These results are consistent with the mice treated with the alloactivated cell vaccine developing a specific response that caused massive lysis of the live cancer cells given in the subsequent challenge.

In another experiment using a different tumor model, C57/BL6 mice (3 per group) were injected subcutaneously with $10^6$ Lewis Lung carcinoma cells alone, mixed with $10^7$ Balb/c×C57 alloactivated lymphocytes cells, or mixed with $10^6$ IL-4 secreting J588L lymphoma cells (allogeneic to C57). The alloactivated cells were prepared by culturing Balb/c splenocytes with C57 splenocytes at a ratio of 10:1 at $3\times10^6$/mL in RPMI 10% FCS for 3 days. All cells were washed in PBS and injected subcutaneously in the flanks of naive C57 mice. Mice were observed for tumor formation, and sacrificed after tumors reached 1 cm in diameter. Mice treated with IL-4 secreting cells survived significantly longer than the other groups with 2 out of 3 long term survivors. The group treated with alloactivated cells alone had no long term survivors.

Correlation of Functional Markers with Antitumor Effect

To determine the correlation between in vitro functional assay results and potential therapeutic benefit, cultures showing various degrees of activation are tested in the mouse lymphoma treatment model. Mixed lymphocyte cultures are set up using splenocytes from a variety of inbred mouse strains at a 10:1 responder:stimulator cell ratio. Alternatively, cultures are set up using a particular responder:stimulator strain combination, but at different cell ratios. After three days of culture, the activity is measured in XTT Formazan assay and esterase assay.

Just before injection, the cultured cells are supplemented with additional splenocytes, as necessary, to normalize the cell ratio, and admixed with $1\times10^6$ live or irradiated J588L lymphoma cells. The preparation is the injected into Balb/c mice, and the effect on survival is monitored. The mice can be rechallenged with a subsequent dose of live lymphoma cells to test for a persisting immunological response. The survival data is then correlated with the functional activity measured during the culture period.

Effect of Alloactivated Cell Composition on Antitumor Effect

As described elsewhere in this disclosure, histamine impairs alloactivation during the lymphocyte culture, as measured in the functional assays. Cimetidine, which is an H2 receptor antagonist, promotes alloactivation. In this study, alloactivation cultures are prepared in the presence or absence of 20 µg/mL histidine or cimetidine, tested in the XTT Formazan and esterase assays, and then injected into Balb/c mice with J588L lymphoma cells to correlate with efficacy.

In another study, the effect of having a plurality of different stimulator or responder cells is tested. Standard cultures containing C57:Balb/c splenocytes (10:1) are compared for efficacy in the mouse lymphoma model with cultures containing: a) C57:Aj:Balb/c splenocytes (9:1:1 or 5:5:1); b) C57:Aj:C3H splenocytes (9:1:1 or 5:5:1); c) C57:Aj:C3H:Balb/c splenocytes (8:1:1:1 or 3:3:3:1).

Example 7

Experiments With Cultured Human Cells

Criteria for Functionality of Alloactivated Cells

The degree of alloactivation (a potential reflection of potency in therapy) can be measured according to the functional assays detailed in Example 5. This example illustrates the degree of activation revealed by the assays.

Human peripheral blood monocytes were isolated from samples taken from a number of unrelated human volunteers, and set up in one-way mixed lymphocyte cultures at a 10:1 responder:stimulator ratio as described elsewhere in this disclosure. The assays were run after 2–3 days in culture.

Figure 6A:
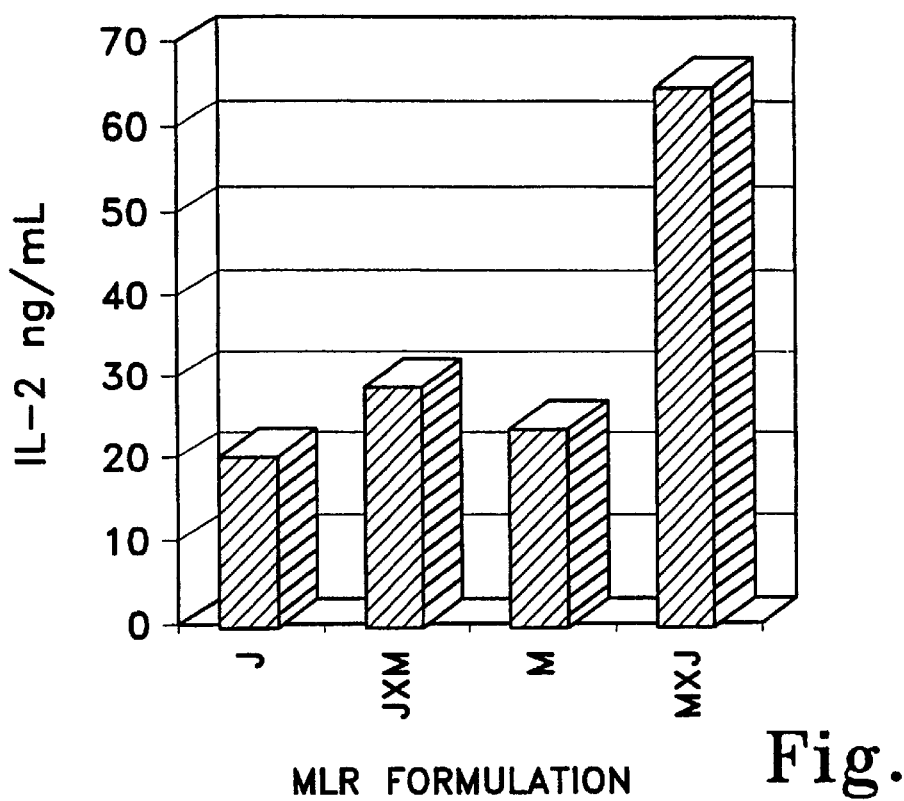
FIG. 6 is a bar graph showing the level of secretion of the cytokines IL-2 and IFN-γ by human alloactivated cell preparations.
Figure 6B:
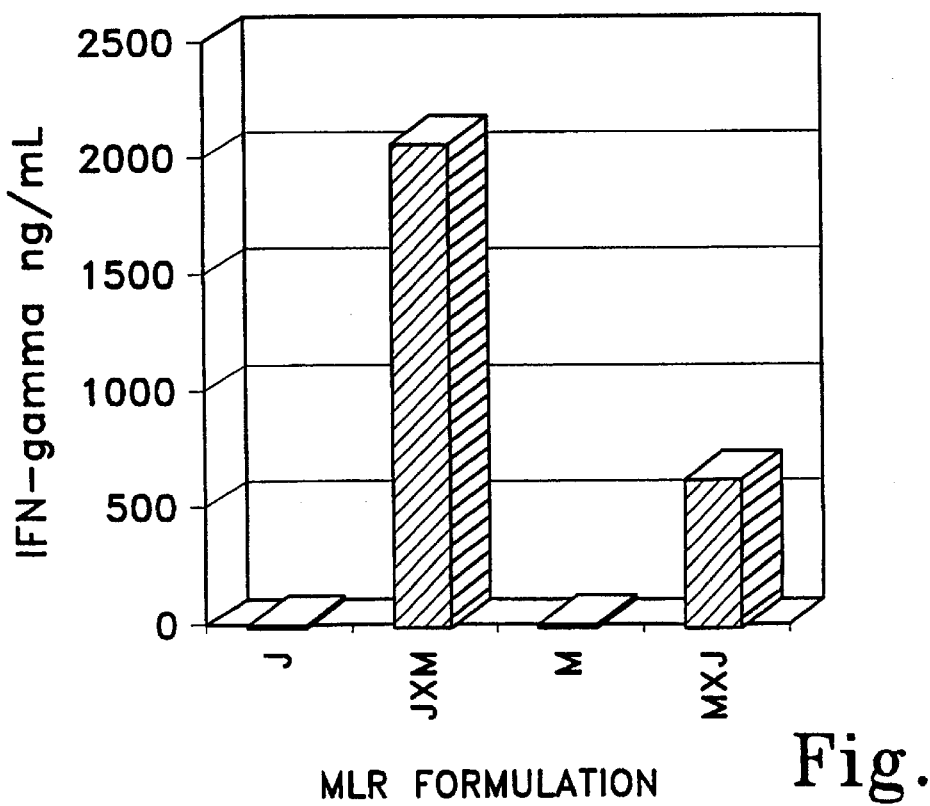

The results are shown in FIGS. 5 and 6. Each of the individuals is indicated by a unique letter, with the responder cells being indicated before the stimulator cells. Thus, the designation A×B means that cells from individual A were cultured with inactivated cells from individual B.

Compared with unstimulated mononuclear cells, alloactivated cells have more esterase activity and reduce more XTT (a Formazan dye). Esterase activity can also be measured by flow cytometry using the esterase substrate, fluorescein diacetate (FDA). T cells with high esterase activity can be identified by Phycoerythrin-labeled CD3 antibody in conjunction with FDA. These measures correlate well with blastogenesis (determined after culturing for one week), or the level of IL-2 or IFN-γ in the supernatant.

Impact of Using Multiple Allogeneic Stimulator Cells

Allo-activated human lymphocyte cultures were produced using cells from either one, two, three or four unrelated donors. $3 \times 10^6$ cells/mL were cultured in 2% FCS-RPMI at 37° C. for 2 days. Two-donor populations were produced by admixing responder cells with stimulator cells at a 10:1 ratio. Populations containing three or four donor cells were produced by mixing responder cells with two or three different stimulator cells at ratios of 9:1:1 or 8:1:1:1.

Figure 7A:
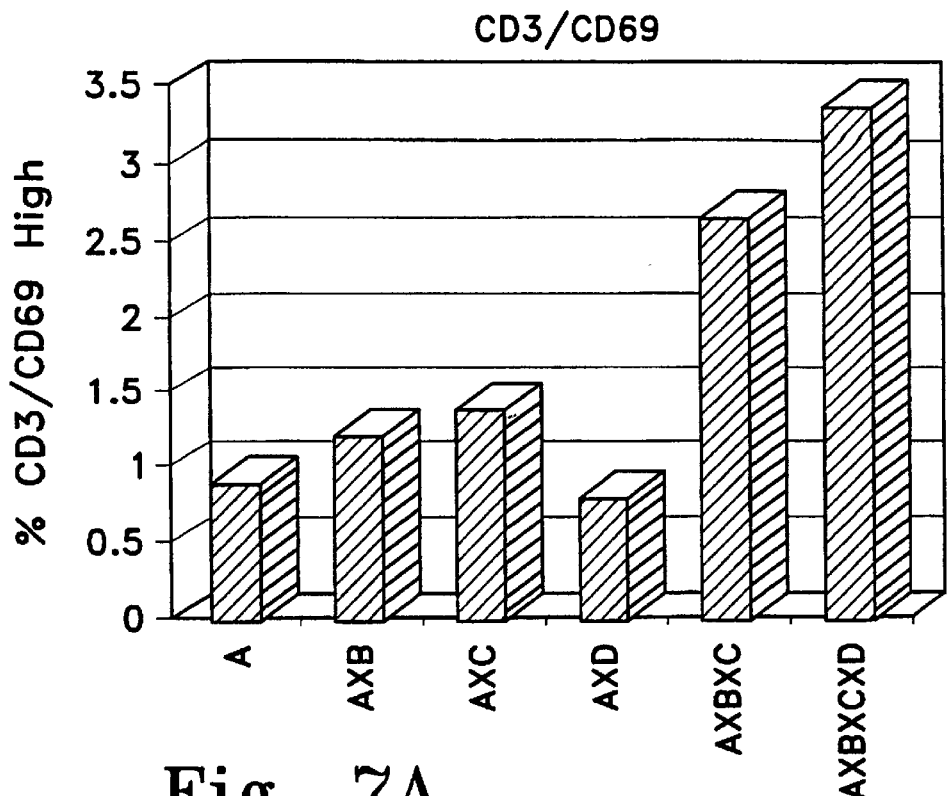
FIG. 7 is a bar graph showing the enhancement of alloactivation of human lymphocytes by using a plurality of different stimulator cells.
Figure 7B:
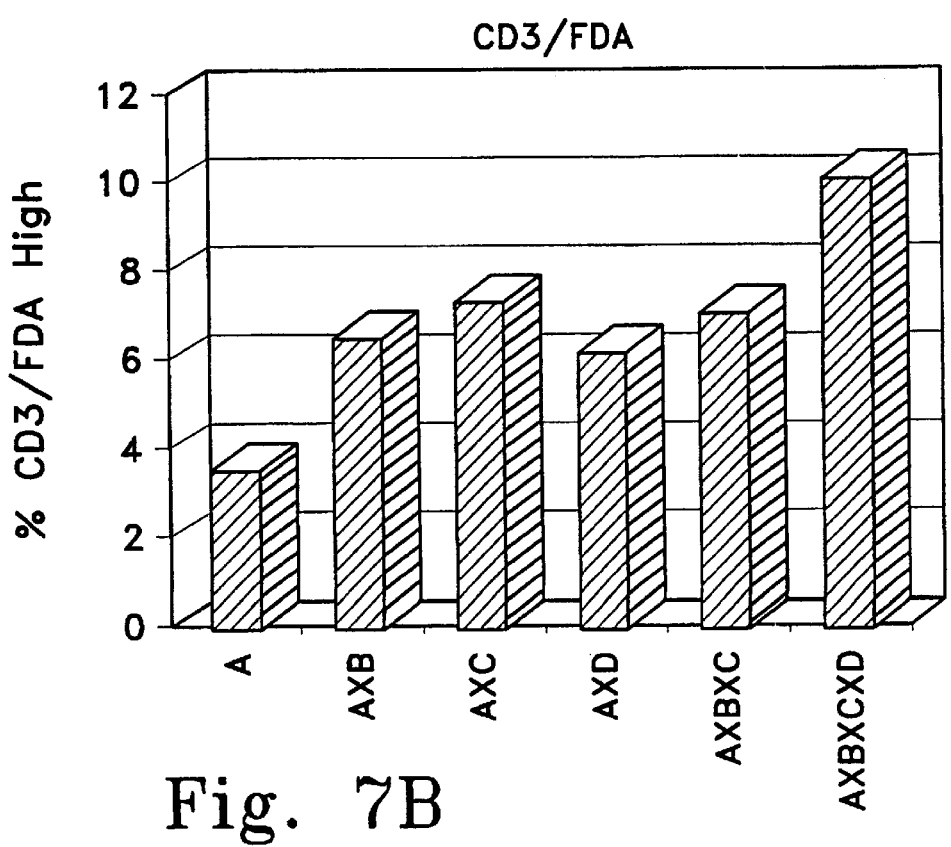

FIG. 7 shows the characteristics of the cells measured using flow cytometry. All values represent percentage of brightly fluorescent cells after counting 4000 cells on a Coulter EPICS XL Cytometer.

The results show that cultures prepared with stimulators from a plurality of donors in certain conditions reach higher levels of activation.

Impact of Altering the Ratio of Responder:Stimulator Cells

Mixed lymphocyte cultures composed of allo-activated human peripheral blood mononuclear cells were produced using cells from the same two unrelated donors at ratios of 10:1, 5:1, or 1:1. Cells were cultured at $0.5 \times 10^6$ cells/mL in 2% FCS-RPMI for 3 days. The strength of these cultures was measured using the XTT Formazan reduction assay.

Figure 8:
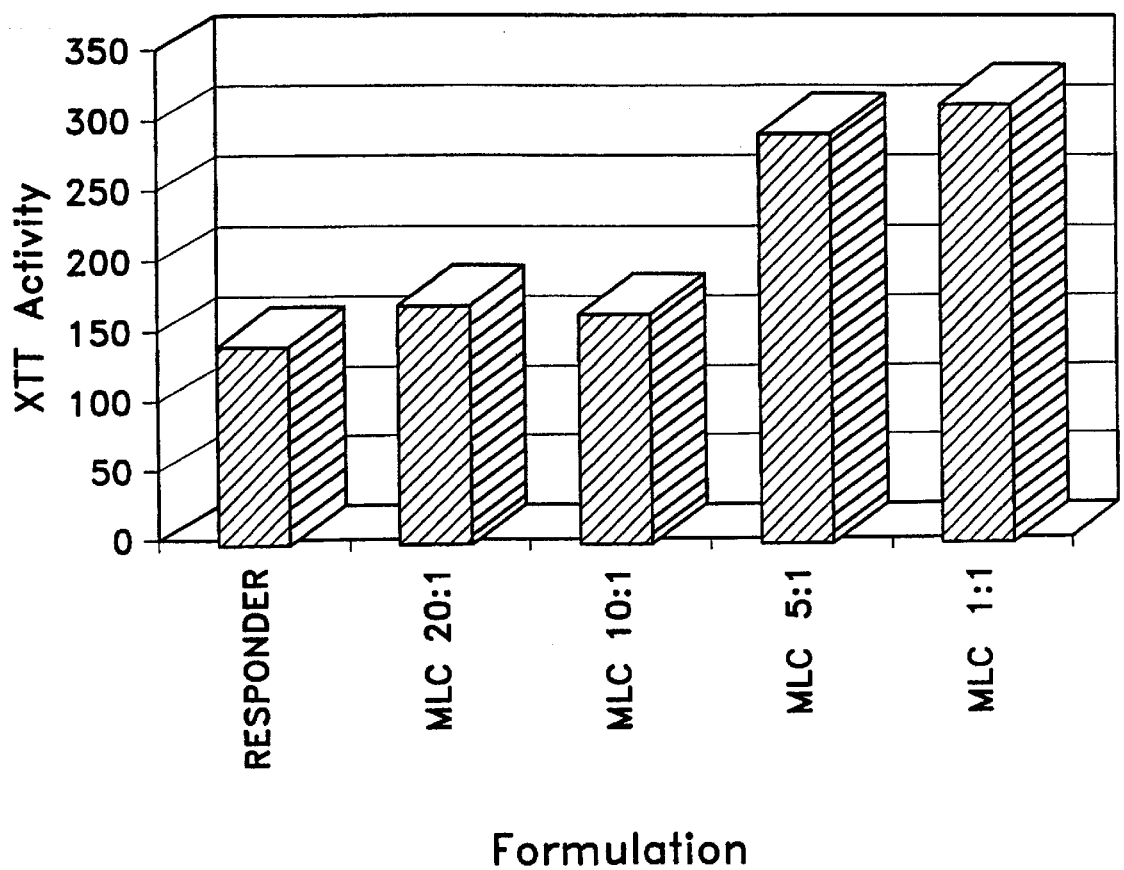
FIG. 8 is a bar graph showing the degree of functional activity of different human alloactivated cell preparations, depending on the ratio of responder:stimulator cells.

The results are shown in FIG. 8

Impact of Histamine or Cimetidine on Alloactivation

Histamine is known to induce the activity of T suppressor cells. Since T suppressor cells can play a role in controlling the activity of the MLR, the effect of histamine and of a potent histamine type 2 (H2) receptor blocking drug, Cimetidine, was tested in alloreacting cell cultures. Cell populations composed of alloactivated human peripheral blood mononuclear cells were produced using cells from unrelated donors. All cultures contain a 10:1 ratio of responder:stimulator mononuclear cells at $0.5 \times 10^6$ cells/mL. In some cultures, 20 µg/mL histamine or 20 µg/ml Cimetidine were added on day 0.

Figure 9:
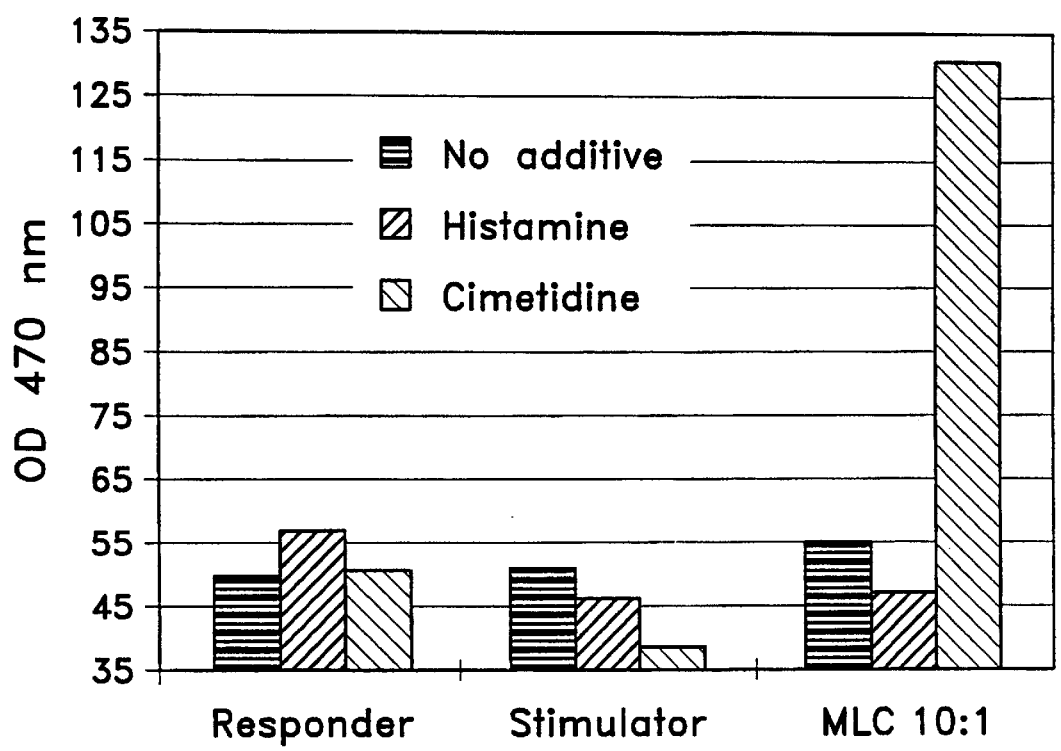
FIG. 9 is a bar graph showing the effect of including 20 μg/mL of histidine (dark shading) or cimetidine (light shading) into cultures of human cells; either the responder alone, the stimulator alone, or mixed cultures at a responder:stimulator ratio of 10:1.

FIG. 9 shows the results measured using a Formazan reduction (XTT) assay. Histamine induced suppression and decreased strength of the allo-activation. Cimetidine enhanced activity, possibly by blocking the development of suppression.

Example 8

Clinical Application of the Cellular Vaccine

This section provides an example showing that an immunological composition comprising activated lymphocytes and autologous cancer cells given subcutaneously is successful in stimulating an immunological response in a primed human recipient.

Cancer patient JT had an aggressive glioblastoma multiforme which had progressed through traditional forms of cancer therapy. She was treated with intratumor implants according to Example 1 in August and September of 1995.

Studies were conducted thereafter to determine whether JT had developed detectable tumor-specific immunity. First, a stable cell line was established from her tumor. Viable tumor cells from a surgically removed tumor were transferred to the laboratory and cultured in RPMI-1640 medium containing 10% fetal calf serum (FCS). The cell line was designated PGA-95. Viable tumor cells were also recovered from subsequently removed occipital lobe, and used to generate a second cell line, designated PGA-96. The two cell lines have similar if not identical characteristics.

MLTC (mixed lymphocyte-tumor cell culture) was performed in the following manner: peripheral blood lymphocytes (PBL) that had been collected and cryopreserved at the time of the August cytoimplant were cultured with viable, growing PGA-95 cells at varying ratios in RPMI-1640/10% FCS for up to 8 days. No anti-tumor activity was detected. However, when PBL obtained from the patient in January 1996 were cultured with PGA-95 cells in an identical manner, a strong anti-tumor cell activity was noted. Virtually 100% of the tumor cells were killed during 7–8 days of coculture at a PBL:PGA-95 ratio of 100:1, as determined by crystal violet staining of adherent tumor cells at the end of the assay. Similar results were obtained at a 50:1 ratio, and about 50% killing of the tumor cells was observed at 10:1. Importantly, no killing of the PGA-95 cells occurred when unrelated (third-party) PBL were used in the coculture instead.

During the first 5 days of MLTC, high levels of IL-2 (1000–1500 pg/mL) were produced, and then fell to much lower levels by day 8. No IL-4 was detected during 8 days of culture. TNF was produced at significant levels only after 6 days, and continued to increase to 400–500 pg/mL by day 8. The phenotype of the responding cells was determined by flow cytometric analysis, and found to be a mixture of CD4+ and CD8+ cells. CD4+ cells proliferated early during culture, followed by proliferation of CD8+ cells. The CD8+ cells did not produce IL-2. Accordingly, the culture medium was supplemented with 200 U/mL recombinant IL-2 (Hoffman-LaRoche), and about $1\times10^9$ CD8+ cytotoxic T lymphocytes (CTL) were generated in about 30 days.

The specificity of the generated CTL was determined by standard $^{51}$Cr release assays. CTL generated against PGA-96 cells efficiently killed both PGA-95 and PGA-96 cells (30–50% lysis in 4–6 h), or cryopreserved tumor cells that had not been previously cultured. The CTL did not kill autologous PBL or autologous fibroblasts; nor did they kill unrelated cancer cell lines: specifically, glioma cells (U373 or ACBT), prostatic adenocarcinoma cells (LNCAP), bladder cancer cells (BLT-2), ovarian carcinoma cells (UCI-107), or leukemia cells (K562).

MLTC was used to monitor the systemic anti-tumor cellular immunity in patient JT as time progressed. Starting in January 1996, blood samples were collected every 2–3 weeks. In the MLTC assay, 100% of the tumor cells were killed at PBL:PGA ratios of 100:1 and 50:1, with proportionately less killing at lower ratios. In April, the activity fell dramatically to the point where only 25% of tumor cells were killed at 100:1, and none at 50:1. It was shortly after this time that the patient developed a recurrence, requiring an occipital lobectomy.

Subsequently, it was decided to attempt to boost her systemic anti-tumor activity by giving her a cutaneous immunization consisting of mixed lymphocytes combined with tumor cells. Cryopreserved cells from the original tumor were inactivated with 10,000 cGy. Cytoimplant cells were prepared by mixed lymphocyte culture of patient's stimulator cells with allogeneic donor responder cells, according to Example 1. The vaccine was prepared by mixing 100, 50, 25, or $10\times10^6$ cytoimplant cells with $1\times10^7$ irradiated tumor cells. The dose range was extrapolated from the animal experiments described in Example 5. The injections were given at four different sites in the back. Cutaneous reactions were noted at all four sites, and the patient developed a febrile response:

response to soluble mediators already present in the cells stimulated in the MLC.

Figure 11:
FIG. 11 is a half-tone reproduction of a photograph taken of the same human patient two days later, showing the delayed hypersensitivity reaction at the four injection sites. The reaction confirms that the patient is responding to components of the vaccine composition.

FIG. 11 is a reproduction of a photograph taken 2 days later, showing evidence of induration. The markings indicate the measured size of the involved area. This evidence of delayed-type hypersensitivity is particularly important, because it suggests that lymphocytes and/or antigen presenting cells have been recruited to the site of the injection by the stimulated allogeneic cells. The allogeneic cells are expected to stimulate the recruited host cells, which in turn should react against the autologous tumor cells also present at the site.

Patient history is shown in Table 7:

TABLE 7

| Date | Observation |
|---|---|
| | 7 yr old right handed caucasian female |
| 10/93 | Biosy-proven glioblastoma multiforme after recurrent seizures. Partial resection performed |
| 11/93 | Tumor progressed. Partial resection performed |
| 11/93 | Tumor progressed. Total resection performed |
| 11/93 | Chemotherapy: 2 courses of cyclophosphamide |
| 2/94 | External beam radiation therapy |
| 6/94 | High dose chemotherapy: cyclophosphamide + melphalan, followed by autologous bone marrow transplant |
| 8/95 | Tumor recurrence. Partial resection performed; residual tumor at ventricular wall |
| 8/95 | First CYTOIMPLANT performed |
| 9/95 | Expanding lesion detected by MRI. Resection performed. Pathology reveals inflammatory changes, necrosis, and small amount of residual tumor |
| 10/95 | Second CYTOIMPLANT performed |
| 12/95 | Gamma knife treatment performed X 2 |
| 2/96 | Treatment with poly IC:LC |
| 4/96 | Tumor progressed. Occipital lobectomy performed. Tumor noted to have crossed midline; not resectable. |
| 5/96 | VACCINE administered subcutaneously. Local immediate hypersensitivity and delayed hypersensitivity observed. Patient develops febrile response. |
| 6/96 | Patient stable and improving neurologically. Tumor not growing. Edema reduced by 50%. MLTC assay for anti-tumor activity is positive, consistent with anti-tumor immune response of host origin. |

MLTC assay performed 12 days after cutaneous administration of the vaccine showed a dramatic return of the immune response to levels noted previously in January–March. MLTC results: have continued at about this level through a determination performed on Jun. 14, 1996. The patient died in about September, 1996.

TABLE 6

| Site & Dose | Features | \multicolumn{6}{c}{Days after Vaccination (Size of involved area in cm × cm)} | | | | | |
|---|---|---|---|---|---|---|---|
| | | 0 | 1 | 2 | 3 | 4 | 5 |
| RUQ $100 \times 10^6$ | Erythema | 2.5 × 2.2 | 1.5 × 1.3 | 1.4 × 1.2 | 0.4 × 0.3 | none | none |
| | Induration | none | 0.5 × 0.4 | 1.0 × 1.1 | 1.0 × 1.0 | 1.4 × 1.7 | 1.3 × 1.6 |
| LUQ $50 \times 10^6$ | Erythema | 2.3 × 2.4 | 1.5 × 1.1 | 1.1 × 0.9 | 0.3 × 0.3 | none | none |
| | Induration | none | 0.5 × 0.3 | 0.7 × 0.6 | 0.8 × 0.8 | 1.4 × 1.8 | 1.2 × 1.2 |
| RLQ $25 \times 10^6$ | Erythema | 1.3 × 1.3 | 1.1 × 1.0 | 0.4 × 0.3 | 0.4 × 0.4 | none | none |
| | Induration | none | 0.2 × 0.2 | 0.3 × 0.3 | 0.3 × 0.4 | 1.0 × 0.9 | 1.0 × 1.0 |
| LLQ $10 \times 10^6$ | Erythema | 0.7 × 0.7 | 0.3 × 0.3 | none | none | none | none |
| | Induration | none | none | 0.1 × 0.1 | 0.3 × 0.4 | 0.8 × 0.7 | 1.0 × 1.0 |
| Clinical Features: | Fever (° F.) | none to 99 | 102 | 104 | 99–100.5 | 99–100.5 | 99–100.5 |
| | Steroids mg/day | 6 | 0 | 10 | 10 | 10 | 10 |

Figure 10:
FIG. 10 is a half-tone reproduction of a photograph of a human patient vaccinated with a combination of mixed lymphocyte culture cells and autologous tumor cells, showing the immediate hypersensitivity reaction at the four injection sites. Doses were: 100×10$^6$ cells (right upper quadrant); 50×10$^6$ cells (left upper quadrant); 25×10$^6$ cells (right lower quadrant); 10×10$^6$ cells (left lower quadrant).

FIG. 10 is a reproduction of a photograph taken of the patient's back shortly after administration of the four injections. Erythema is apparent at each injection site; likely a Further trials are conducted to verify the parameters of the vaccination protocol. Patients with grade III or IV astrocytoma are recruited into studies conducted under the auspices of the appropriate Institutional Review Board, as in Example 1. All patients are enrolled with informed consent, and randomized into the various treatment groups.

Tumor cells are cryopreserved from each patient at the time of surgery, and proliferated ex vivo if necessary to obtain sufficient cells for the anticipated course of therapy. Thawed or cultured tumor cells are subjected to 10,000 rads of gamma irradiation. Preparative-scale mixed lymphocyte cultures using inactivated patient stimulator cells and donor leukocytes are conducted essentially as described in Example 1.

In one trial, patients are given two vaccinations two weeks apart. The mononuclear cells used to prepare each cellular vaccine are obtained from two healthy, unrelated donors. Donors prescreened to minimize risk for infectious diseases, and those that test positive are eliminated. Screening includes testing for antibody specific for HIV-1, HIV-2, HTLV-I, HTLV-II, hepatitis C, or hepatitis B core; HIV antigen, HBsAg, RPR, or elevation in liver markers such as ALT. HLA-A, -B, -C, and -DR typing is performed to select donors allogeneic to the patient and to each other. By using genetically disparate donors, the likelihood of hyperacute rejection of the second administration is decreased. In addition, each injection is preceded by testing the major cross-match (donor cells and patient's serum) for the presence of pre-formed antibody. Matching of blood types is generally not required, except that administration of cells from an Rh-positive donor to an Rh-negative female of reproductive age or younger is avoided where possible.

The mixed lymphocyte culture is conducted by mixing donor and inactivated patient peripheral blood mononuclear cells at a ratio of 10:1, and culturing at $3 \times 10^6$ cells/mL in AIMV supplemented with 2% fetal calf serum for 3 days at 37° C. The total number of mononuclear cells required for a single inoculum is no more than $1 \times 10^9$. The stimulated cells are collected and washed by centrifugation, then suspended in sterile, injectable saline. Quality control of the production of activated cells includes monitoring cell counts and viability, testing for mycoplasma and endotoxin, and monitoring for lymphocyte activation using early activation markers.

Before use in treatment, the alloactivated cell preparation is also evaluated according to functional release criteria. The Tetrazolium Reduction Assay (XTT) described in Example 5 is conducted on a cell sample. Flow Cytometry is conducted to measure cell surface expression of CD69 using fluorescent antibody; or increased intracellular esterase activity using fluorescein diacetate. Cultured cells are considered to be sufficiently activated if the level measured in either one (but preferably both) of these assays is $\geq 10\%$ above unstimulated donor control value on any day of the culture period (day 1, day 2, or day 3). Once the culture passes the criteria, testing on subsequent days is not needed. The cells are harvested on day 3, mixed with the requisite number of primary or cultured tumor cells, and prepared for human administration.

Patients first recruited into the study receive one of three graded dosages in two injections separated by two weeks ($10^8$ MLC cells: $10^8$ tumor cells): Group 1 is given $1 \times 10^8$ MLC cells; Group 2 is given $5 \times 10^8$ MLC cells; Group 3 is given $1 \times 10^9$ MLC cells. The MLC cells are mixed with between $1 \times 10^6$ and $1 \times 10^7$ tumor cells derived from the patient for each innoculum, depending on the number available, and tending towards $1 \times 10^7$ where possible. The inoculations are administered subcutaneously using a 20–21 gauge needle, 10 cm inferior to the inguinal ligament on the anterior mid thigh on opposite sides. The maximum tolerated dosage (MTD) is determined as follows: If at least one of three patients receiving a given cell combination develops reversible Grade 3 or irreversible Grade 2 toxicity, up to three additional patients are entered at the same dose. If a second patient develops the same degree of toxicity or higher, the cell combination is defined as the MTD. Otherwise, dosages are escalated until the maximum level is reached.

Clinical response is monitored by several criteria, including local induration, pruritus, or necrosis at the injection site; systemic effects such as fever, malaise, headache, and altered hematological or renal parameters; and tumor volume detected by such criteria as MRI. The results from MRI are interpreted cautiously. A growing tumor mass (a feature of progressive disease) or local leukocyte induration (a possible feature of successful treatment) may both appear as an enlarging area on MRI. However, a reduction in the area is consistent with shrinking tumor mass and successful treatment.

The presence of a cellular immune response in the treated patient is monitored by several criteria. Patient lymphocytes obtained before and after each inoculation are cultured with irradiated allogeneic cells of donor origin or from a third party (for anti-allotype response), or irradiated patient tumor cells, or third-party tumor cells (for specific anti-tumor response). The response of patient lymphocytes in culture is determined by measuring proliferation using reduction of MTT or one of the other functional assays as a surrogate marker for cellular division. Expression of CD69 is determined by immunofluorocytometry using PE-labeled antibody.

Optionally, the responding T cells are costained for CD4, CD8, or CD31 to identify helper or suppressor subsets, or for CD45RF to distinguish $T_{H1}$ from $T_{H2}$ cells. Cytokines IL-2, IL-4, IFN-γ and TNF-α secreted into the culture media are quantified by ELISA. IL-2 and IFN-γ correlate with $T_{H1}$ activity, IL-4 correlates with $T_{H2}$ activity, and TNF-α correlates with the activity of both.

Patients' PBL are also tested for their ability to respond to autologous tumor cells, as described earlier in this example. PBL are cultured in the presence or absence of tumor cells, and then measured for the degree of responsiveness. General T cell activation can be measured by the functional assays described in Example 5, [$^3$H] thymidine incorporation, or blastogenesis. Cytotoxic T cell activity can be measured as cytolysis of $^{51}$Cr labeled tumor cells. The effective delayed type hypersensitivity (DTH) anti-tumor response in the treated patient is measured by comparing the 48-hour response of the intradermal administration of $5 \times 10^5$ autologous tumor cells, mumps, tricophyton, or PPD antigens with that observed for the same series before treatment.

In a subsequent trial, vaccine therapy is combined with implant therapy. At the time of surgical debulking, an implant of allogeneic lymphocytes stimulated with autologous stimulator cells is placed into the tumor bed as described in Example 1. The removed tumor cells are frozen and/or cultured for preparation of a cellular vaccine. Two donors are selected who are allogeneic to the patient, and preferably allogeneic to each other and the cell donor for the implant. Each donor's cells is used to prepare the MLC component of a vaccine as described earlier in this example, and then mixed with patient's tumor cells. One vaccine is administered at 4 weeks following the implant; the second at 6 weeks. The dosage selected is at or below the MTD established in the preceding trial. Clinical and immunological criteria are monitored as before.

The response of patients undergoing the combined therapy is compared with that of patients receiving an intracranial implant alone, to determine the degree to which prior vaccination enhances the effectiveness of the implant.

Another study is conducted on patients with Stage IV (metastatic) colon cancer. Patents are enrolled in the study under terms of informed consent, and undergo a standard colectomy. About 1 week later (around the time they are discharged from the hospital), they begin a course of four vaccine injections.

The vaccine composition consists essentially of an alloactivated cell population mixed with tumor cells. Patients receive one of three different doses: $1 \times 10^8$ MLC cells; $3 \times 10^8$ MLC cells; or $1 \times 10^9$ MLC, mixed with up to $1 \times 10^7$ inactivated tumor cells, depending on availability. The same dose is given four times on a weekly schedule.

Initial studies are conducted primarily to determine the maximum tolerated dose (MTD). Undesirable clinical side effects at the injection site include an unacceptable level of induration, inflammation, or ulceration.

Once the MTD is determined, a comparison is made between the 4-week vaccination schedule alone, and a vaccination course initiated by direct implantation into a tumor mass. The implant group is treated two days to a week after colectomy, using ultrasound to guide an injection needle into a sizeable metastatic tumor mass in the liver. The metastatic site is injected with a preparation of $10 \times 10^9$ MLC alloactivated cells alone, suspended in a minimum volume of saline. Beginning one week later, the patients in this group also receive the 4-week course of the MLC-tumor cell vaccine.

The patients are monitored for the extent of the clinical and immunological response for at least three months following therapy. Immunological criteria are followed as described above. Clinical criteria is followed, in part, by tracking the volume of tumor metastasis present in the liver. A CT scan is performed at regular intervals, the volume of each metastatic site is calculated, and the volumes are compared with the measurements obtained before treatment. Progression of disease is indicated by an increase in volume of the metastasis, or an increase in the number of metastatic sites. A successful outcome is indicated by reversal of the disease, or slower progression in comparison with the typical outcome for patents with colon cancer of the same grade.

Example 9

Commercial Production of Alloactivated Cell Compositions

This protocol describes the overall approach to production of the mixed lymphocyte culture. The design of this methodology takes into account Good Manufacturing (GMP) and Good Laboratory (GLP) Practices, and complies with requirements of Code 21 of U.S. Federal Regulations.

Patient peripheral blood mononuclear cells, at least $2 \times 10^9$ cells are collected by modified leukapheresis from the patient to be treated. Isolation of cells is performed on a Baxter Fenwall apheresis machine or equivalent machine using the Stem Cell Collection Procedure. Cells are shipped in a Baxter-type component bag on ice (4–10° C.). Transit temperature is monitored using MONITOR-MARK™ Time/Temperature Tags.

Donor peripheral blood mononuclear cells, at least $10 \times 10^9$ cells, are collected by modified leukapheresis from a healthy individual. Isolation of cells is performed on a Baxter Fenwall apheresis machine or equivalent ,using the Stem Cell Collection Procedure. Donors are unrelated, anonymous, and random individuals, picked from a list of prescreened potential donors.

Prescreening of the donors should indicate negative risk factors for HIV, Hepatitis, Spongioform Encephalitides, or Tuberculosis. Each cell component is tested negative for HIV 1/2 Ab, HIV Ag, CMV Ab, HTLV I/II Ab, HCV Ab, HBcAb, HBsAg and RPR. Cells are shipped in a Baxter-type component bag on ice (4–10° C.).

Upon receipt each component is tested for sterility, appropriate cell counts, and viability. Components are maintained at 4–10° C. until use, and used or frozen within 72 hours of collection. Thawed frozen material are used within 2 hours and not re-frozen. Pre-clinical studies indicate that components stored at 4° C. in ACD anticoagulated plasma or material frozen in DMSO-containing media are suitable for the production of effective cell compositions.

Plasma is removed form both the donor and patient components by centrifugation. Donor plasma may be collected and heat-inactivated for use as a medium supplement. Component cells are suspended in small volumes of PBS and appropriate volumes of each suspension is mixed to produce a culture that contains $3 \times 10^6$ mononuclear cells/ml in AIMV medium at a ratio of 10:1 to 20:1 (donor:patient cells). Heat-inactivated donor plasma is added to a final concentration of 2%. Mixed cells are pumped into Fenwall 3 liter gas permeable culture bags through the use of the Fenwall solution pump and sterile set-up. Samples of the component cells may also be set up in small culture tubes for testing of lymphocyte activation. Testing of functional activity is compared with control cultures containing unstimulated donor cells alone.

Cell mixtures are cultured in a ISO-°9000 Forma 37° C. incubator with 5% humidified and HEPA filtered $CO_2$ for 3 days, and closely monitored. Cells are harvested after culture by centrifugation. Samples are taken for quality assurance assays. Each preparation is tested for final sterility, adequate cell counts, adequate viability and functional activity.

The cell preparation is suspended in sterile 25% human albumin, and placed in sterile injectable vials for transport. Each preparation is labeled with an expiration date and time, which is 30 hours after packaging, and accompanied by appropriate instructions, release specification results, and a MONITOR-MARK™ Time/Temperature Tag. Cell preparations are packaged and shipped via overnight courier service. If not used immediately, the cells are stored in a refrigerator at 4–10° C. Any preparation not implanted before the expiration date is discarded.

In process tests that measure product consistency include:

pre-screen infectious disease tests;

in process and final product sterility tests;

final product mycoplasma and endotoxin;

in process and final product cell counts; in process and final product viability ($\geq 85\%$).

Cells must also meet satisfactory fictional criteria. Preparations not meeting any of these criteria are not used for treating patients.

TABLE 8

Donor and Patient Screening
(At Time Of Leukapheresis Procedure)

| TEST | METHOD (AS PER HOSPITAL BLOOD BANK SOPS) | SPECIFICATION |
|---|---|---|
| Pre-screen for risk factors | HIV<br>Hepatitis<br>Spongioform encephalitis<br>Tuberculosis | Report Only |
| Adventitious agent screening | HIV 1 and 2 Ab<br>HIV Ag<br>HBs-Ag<br>HBc Ab*<br>HCV Ab<br>HTLV 1 and 2 Ab<br>CMV Ab*<br>RPR | All negative* |

*Patient may be positive for HBcAb or CMV Ab, and components are labeled as such. If CMV negative donor components are not available, a CMV Ab positive donor component may be used, even for CMV negative patients.

TABLE 9

Pre-Process Testing Of Donor And Patient Mononuclear Cells
(At Time Of Receipt At Facility, Prior To Irradiation
Of Patient Mononuclear Cells)

| TEST | SPECIFICATION |
|---|---|
| Sterility | Sterile |
| Cell Count | |
| Patient | $\geq 2 \times 10^9$ cells |
| Donor: | $\geq 10 \times 10^9$ cells |

TABLE 10

In Process Testing Of Alloactivated Cells

| TEST | ASSAY | SPECIFICATION |
|---|---|---|
| Bioactivity of lymphocytes activation (Tests on days 1, 2, and/or 3 of culture) | Tetrazolium Reduction Assay (XTT) | $\geq 10\%$ above unstimulated donor control value on any day of test |
| | Flow Cytometry (cell surface expression of CD69 by fluorescent antibody; or increased intracellular esterase activity by fluorescein diacetate) | $\geq 10\%$ above unstimulated donor control value on any day of test |

TABLE 11

Final Product Testing

| TEST | SPECIFICATION |
|---|---|
| Sterility | Sterile |
| Cell Count | $9 \times 10^9$ cells ($\pm 10\%$) |
| Viability | $\geq 85\%$ viable cells |
| Mycoplasma | Negative (results not available until after the implantation) |
| Endotoxin | $\leq 350$ EU/total body |

Although the foregoing invention has been described in some detail by way of illustration and example for purposes of clarity and understanding, it will be apparent to those skilled in the art that certain changes and modifications may be practiced. Therefore, the description and examples should not be construed as limiting the scope of the invention, which is delineated by the appended claims.

What is claimed as the invention is:

1. An immunogenic composition suitable for administration to a human, comprising an effective combination of:
    a) stimulated lymphocytes allogeneic to the human; and
    b) tumor-associated antigen from the human;
    wherein the combination is effective to elicit an immune response to the tumor-associated antigen in the human subject after administration.

2. The immunogenic composition of claim 1, wherein said tumor-associated antigen is comprised in a primary tumor cell from said human, or a progeny of such a tumor cell obtained by culturing the tumor cell ex vivo.

3. The immunogenic composition of claim 1, wherein said tumor-associated antigen is comprised in an extract of a primary tumor cell from said human, a progeny of a primary tumor cell from said human, or a combination thereof.

4. The immunogenic composition of claim 1, wherein said stimulated lymphocytes have been stimulated by culturing with leukocytes allogeneic to the lymphocytes.

5. The immunogenic composition of claim 1, where said stimulated lymphocytes have been stimulated by culturing with a recombinantly produced cytokine, a mitogen, or with a cell genetically altered to secrete a cytokine at an elevated level.

6. An immunogenic composition suitable for administration to a humans, comprising an effective combination of:
    a) lymphocytes allogeneic to the human;
    b) leukocytes allogeneic to the lymphocytes; and
    c) an inactivated tumor cell population, consisting essentially of primary tumor cells obtained from the human, or the progeny of such cells;
    wherein the combination is effective to elicit an immune response to the tumor cell population in the human subject after administration.

7. The immunogenic composition of claim 6, wherein the leukocytes are autologous to the human.

8. The immunogenic composition of claim 6, wherein the leukocytes are allogeneic to the human.

9. The immunogenic composition of claim 6, comprising leukocytes from at least three different human donors.

10. The immunogenic composition of claim 6, wherein the inactivated tumor cell population are selected from the group consisting of melanoma, pancreatic cancer, liver cancer, colon cancer, prostate cancer, and breast cancer cells.

11. The immunogenic composition of claim 6, wherein the leukocytes are inactivated.

12. The immunogenic composition of claim 6, wherein said lymphocytes comprise a cell that has been genetically altered to express a cytokine at an elevated level.

13. The immunogenic composition of claim 6, wherein said leukocytes and said lymphocytes are cocultured for a duration and under conditions sufficient for allogeneic stimulation of the lymphocytes, prior to combination with said tumor cell population.

14. The immunogenic composition of claim 6, wherein said coculturing is for a duration and under conditions sufficient to stimulate elevated cytokine secretion by the lymphocytes.

15. A unit dose of the immunogenic composition according to claim 6, wherein the number of said lymphocytes allogeneic to the leukocytes in the dose is between about $1 \times 10^8$ and $2 \times 10^9$.

16. A unit dose of the immunogenic composition according to claim 6, wherein the inactivated tumor cell population in the dose consists of between about $1 \times 10^6$ and $5 \times 10^7$ cells.

17. A method for producing the immunogenic composition of claim 1, comprising mixing:
   a) stimulated lymphocytes allogeneic to said human; with
   b) tumor-associated antigen from the human.

18. A method for producing the immunogenic composition of claim 1, comprising mixing:
   a) cells obtained from a coculture of lymphocytes allogeneic to said human and leukocytes allogeneic to the lymphocytes; with
   b) primary tumor cells from the human, or progeny thereof.

19. A kit for producing the immunogenic composition of claim 1, comprising in separate containers:
   a) stimulated lymphocytes allogeneic to the human; and
   b) tumor-associated antigen from the human.

20. A kit for producing the immunogenic composition of claim 1, comprising in separate containers:
   a) cells obtained from a coculture of lymphocytes allogeneic to said human and leukocytes allogeneic to the lymphocytes; and
   b) primary tumor cells from the human, or progeny thereof.

21. A method for inducing an anti-tumor immunological response in a human, comprising administering an immunogenic amount of the immunogenic composition of claim 1 to the human.

22. A method for inducing an anti-tumor immunological response in a human, comprising administering an immunogenic amount of the immunogenic composition of claim 6 to the human.

23. A method for stimulating an anti-tumor immunological response in a human, comprising the steps of:
   a) mixing ex vivo a first cell population comprising tumor cells, and a second cell population comprising lymphocytes allogeneic to the human, to produce a cell mixture; and
   b) administering an immunogenic amount of the cell mixture to the human.

24. The method of claim 23, wherein said tumor cells comprises cells selected from the group consisting of melanoma, pancreatic cancer, liver cancer, colon cancer, prostate cancer, and breast cancer.

25. The method of claim 23, wherein said second cell population further comprises leukocytes allogeneic to the lymphocytes.

26. The method according to claim 23, wherein the second cell population contains leukocytes from at least three different human donors.

27. The method of claim 23, wherein the leukocytes are autologous to the human.

28. The method of claim 23, wherein the leukocytes are allogeneic to the human.

29. The method of claim 23, wherein said immunological response is a primary response.

30. The method of claim 23, wherein said immunological response is a secondary response.

31. The method of claim 23, wherein said human has been previously treated by administration of alloactivated allogeneic lymphocytes into a solid tumor in the human or at or around a site where a solid tumor or a portion thereof has been removed.

32. A method for treating a neoplastic disease in a human, comprising administering an effective amount of the immunogenic composition of claim 6 to the human.

33. A method for treating a neoplastic disease in a human, comprising the steps of:
   a) mixing ex vivo a first cell population comprising tumor cells, and a second cell population comprising lymphocytes allogeneic to the human, to produce a cell mixture; and
   b) administering an effective amount of the cell mixture to the human.

34. The method of claim 33, wherein said second cell population further comprises leukocytes allogeneic to the lymphocytes.

* * * * *